(12) United States Patent
Lippitt et al.

(10) Patent No.: US 7,041,108 B2
(45) Date of Patent: May 9, 2006

(54) GRASPER MECHANISM WITH BIASED FIXED FLEXURE ELEMENTS

(75) Inventors: Robert G. Lippitt, Smithfield, NC (US); Raymond F. Lippitt, Bethesda, MD (US); Andrew R. Leopold, Lake Zurich, IL (US)

(73) Assignee: Lippitt Extractor Company, LLC, Smithfield, NC (US)

( * ) Notice: Subject to any disclaimer, the term of this patent is extended or adjusted under 35 U.S.C. 154(b) by 163 days.

(21) Appl. No.: 10/436,445

(22) Filed: May 13, 2003

(65) Prior Publication Data

US 2004/0092957 A1 May 13, 2004

Related U.S. Application Data

(60) Provisional application No. 60/386,190, filed on May 28, 2002.

(51) Int. Cl.
*A61B 17/22* (2006.01)

(52) U.S. Cl. ...................... 606/127; 606/127; 606/128; 606/106; 606/25; 606/110; 606/113; 604/264; 604/265

(58) Field of Classification Search ........ 606/127–128, 606/106, 110, 113; 604/264–265; 24/530, 24/535–537
See application file for complete search history.

(56) References Cited

U.S. PATENT DOCUMENTS

| | | | | |
|---|---|---|---|---|
| 5,906,622 | A | * | 5/1999 | Lippitt et al. ............... 606/127 |
| 5,924,175 | A | * | 7/1999 | Lippitt et al. .................. 24/537 |
| 6,743,228 | B1 | * | 6/2004 | Lee et al. ...................... 606/47 |

* cited by examiner

*Primary Examiner*—Corrine McDermott
*Assistant Examiner*—Christopher Prone
(74) *Attorney, Agent, or Firm*—Brinks Hofer Gilson & Lione

(57) ABSTRACT

An expansible and retractable mechanism of the type disclosed in U.S. Pat. No. 5,924,175 and/or a medical grasper of the type disclosed in U.S. Pat. No. 5,906,622 in which (1) the fixed flexure elements are self-biased to move into the expanded condition thereof. A handpiece for the medical grasper is constructed and arranged so that after a stone has been grasped, a further digital pull on the movable handpiece structure effects the application of a limiting resiliently yielding force to the gripping action.

2 Claims, 18 Drawing Sheets

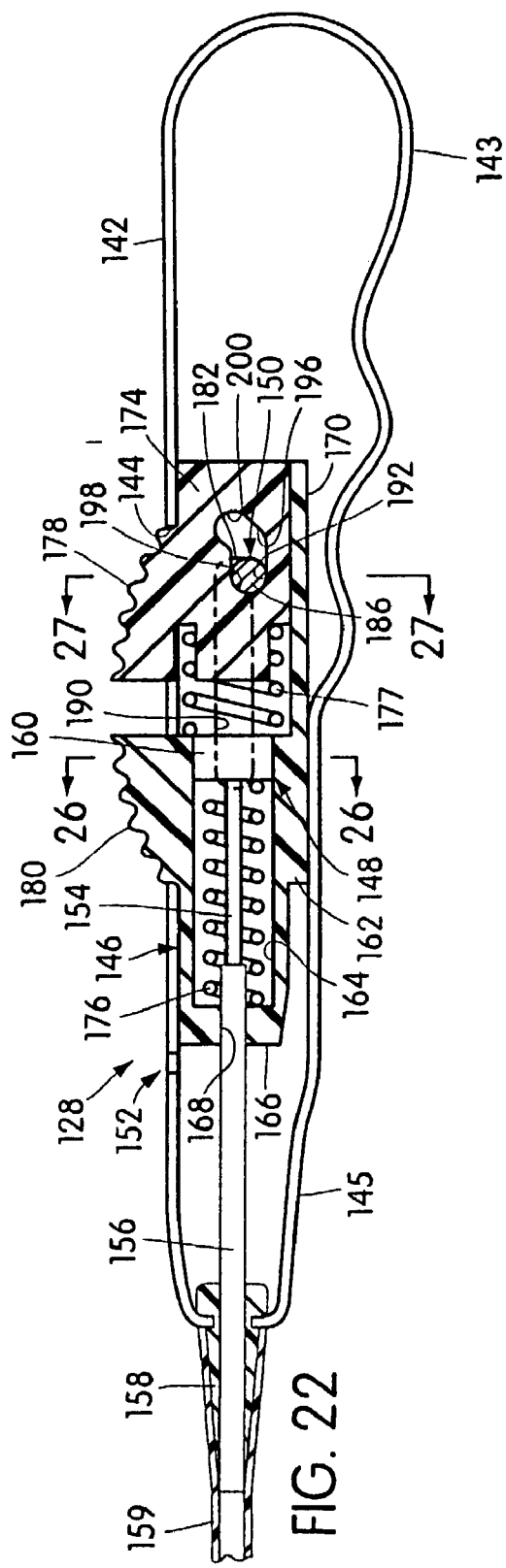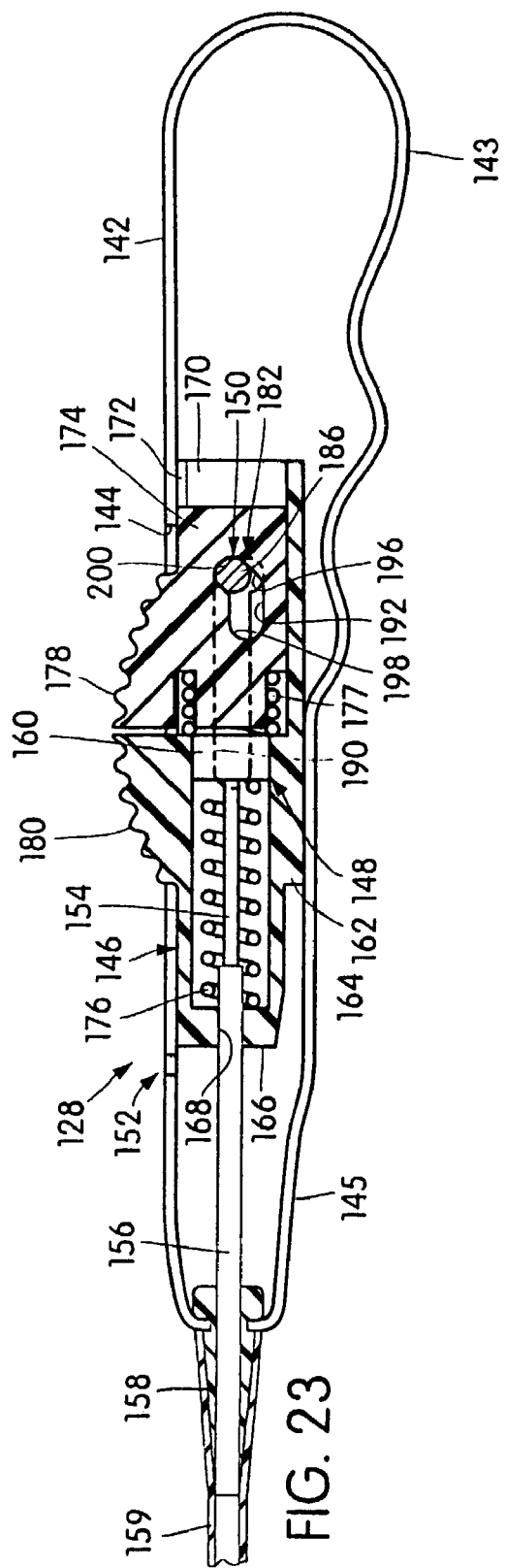

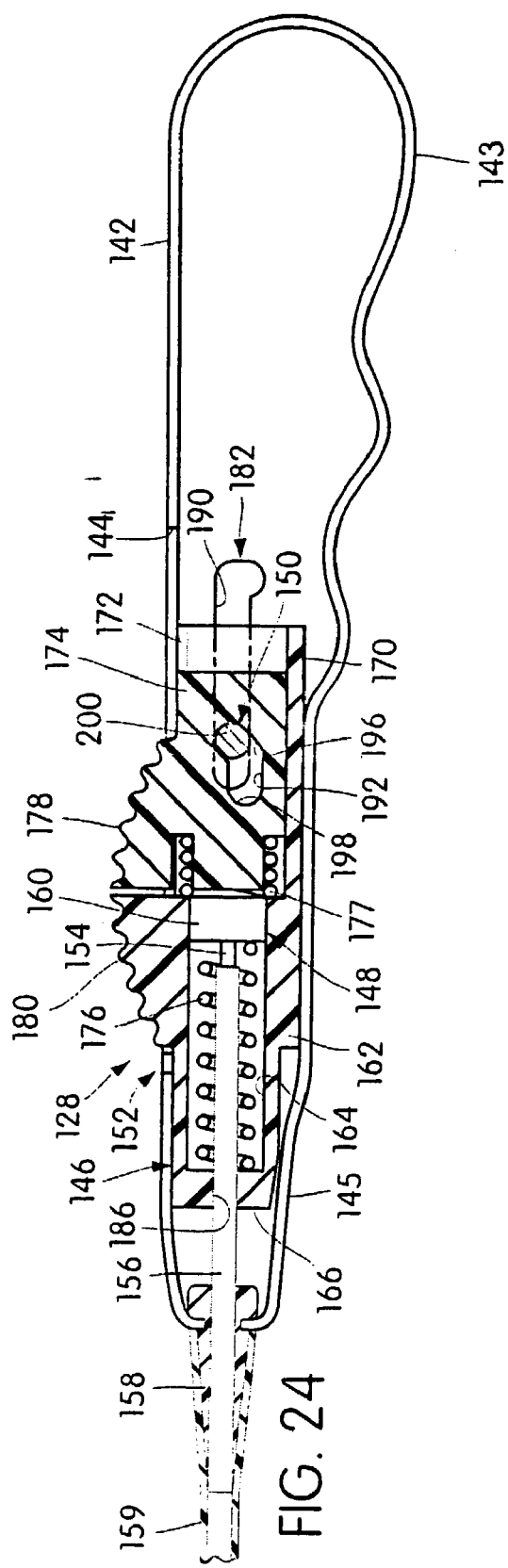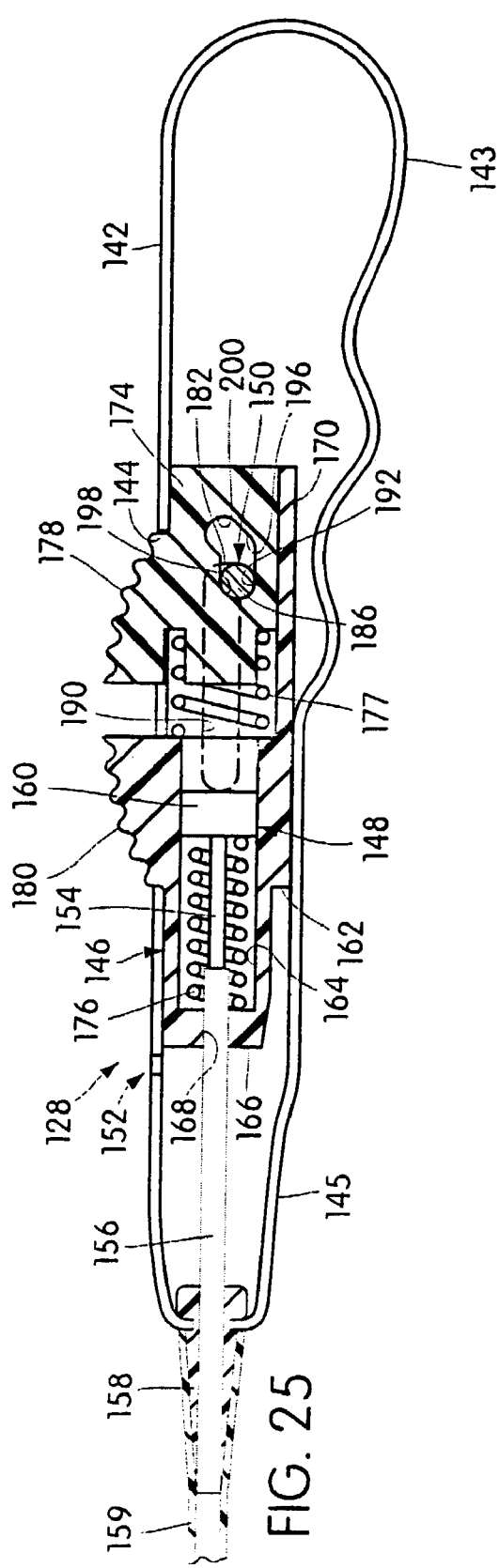

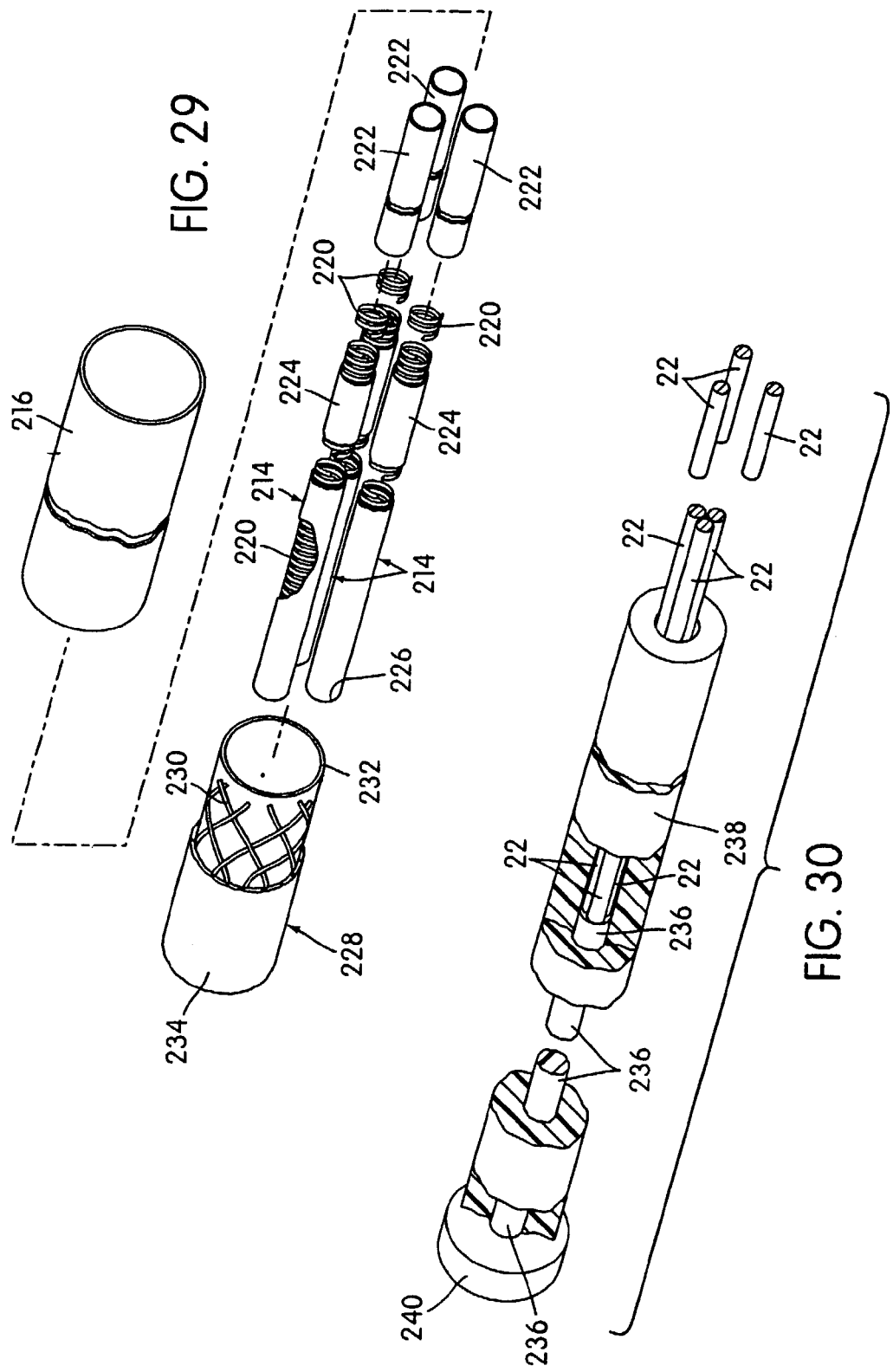

GRASPER MECHANISM WITH BIASED FIXED FLEXURE ELEMENTS

The subject matter of the application elates to improvements in mdical extractors or graspers of the type disclosed in U.S. Pat. Nos. 5,906,622 and 5,924,175, the disclosure of both of which is hereby incorporated y reference into the present specification. The present application claims priority from provisional application Ser. No. 60/386,190 filed may 28, 2002, the disclosure of which is hereby incorporated by reference into the present specification.

BACKGROUND OF HE INVENTION

The grasper disclosed in the '622 patent comprises an elongated cannula assembly having an annularly expanding and retracting gripping and releasing mechanism at the distal end thereof and a moving assembly at the proximal end thereof. The gripping and releasing mechanism as described in both the '622 patent and the '175 patent includes an annular series of longitudinally fixed flexure elements and a corresponding series of longitudinally movable flexure elements. The moving assembly is operable to effect a relative movement between the flexure elements to move them between a retracted condition and an expanding condition defined by an annular series of transversely outwardly flexed fixed elements inerconnected by an annular series of arcuately flexed portions of said flexure elements.

BRIEF SUMMARY OF THE INVENTION

The present invention embodies improvements in the medical extractor disclosed in the '622 patent and the expanding and retraction mechanism of the patent. The feature of one improvement is to self bias the fixed flexure elements to move into the expanded condition thereof.

Other improvements include (1) the provision of a bendable section of the cannula assembly at the distal end thereof adjacent the gripping and releasing mechanisms in which the flexible tube sections hereof are contained in non-adhered relation y an overlying flexible sleeve and (2) the provision of a handpiece assemle capable of limiting the force of the pull that can e manually applied to retain a stone in gripped relation by allowing for a resiliently yielding movement after ripping has been accomplished. Preferably, the handpiece is provided with a lock srstructure enabling the gripping action to be maintained within the limiting force while allowing the manual pull to be removed.

DESCRIPTION OF THE DRAWINGS

FIG. 22 is a view similar to FIG. 2 showing a moving assembly of modified form constructed in accordance with the principles of the present invention;

FIG. 23 is a view similar to FIG. 22 showing the position of the parts when in an initial unlocked position;

FIG. 14 is a view similar to FIGS. 22 and 23 showing the parts in a position corresponding to the position of FIG. 4;

FIG. 25 is a view similar to FIGS. 22 an 23 showing the parts in a position corresponding to the position of FIG. 6;

FIG. 29 is a view similar to FIG. 28 showing another form of the device embodying the principles of the present invention; and FIG. 30 is another modification within the present invention which is useful with the modified form shown in FIG. 29.

DESCRIPTION OF THE PREFERRED EMBODIMENT

Figure 1:
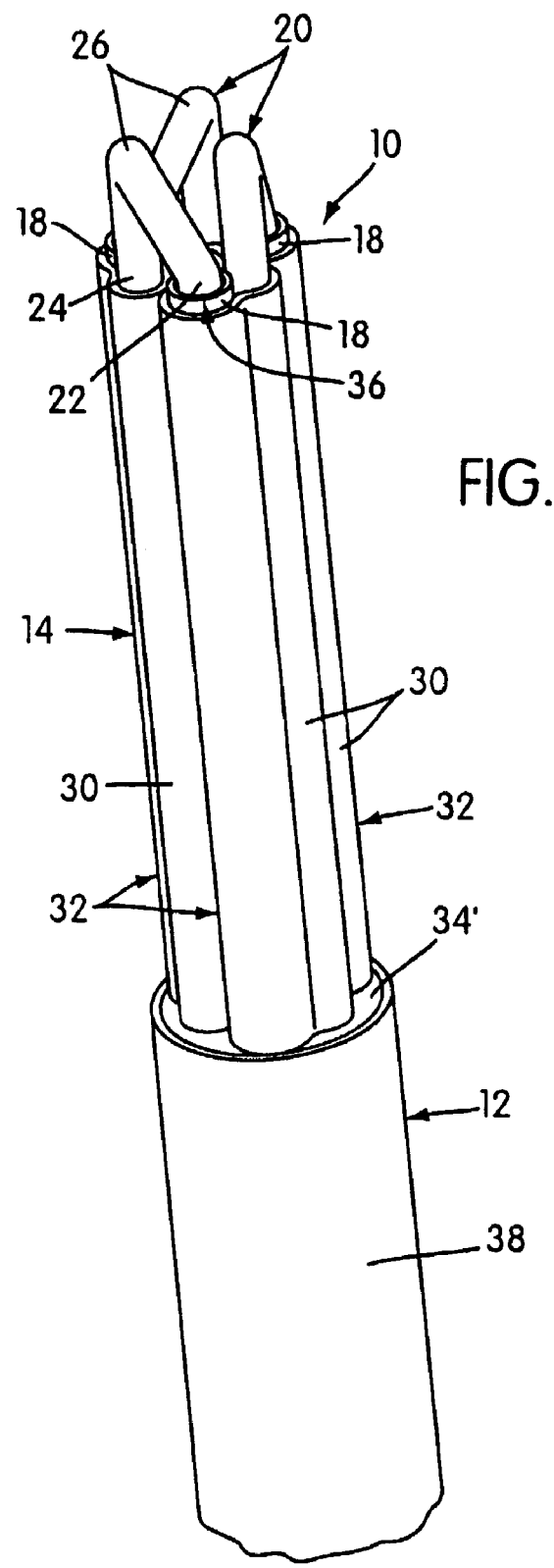
FIG. 1 is a fragmentary prspective view looking down aon the distal end of the gripping and releasing mechanism and adjacent portion of the cannula assembly of a medical extractor embodying he principles of the present invention, the parts being shown in a closed position.

Referring now more particularly to FIGS. 1–21 of the drawings, there is shown therein a medical extractor, generally indicated at 10, embodying the principles of the present invention. The medical extractor 10 as shown includes, in general, an elongated cannula assembly, generally indicated at 12, having an expandable and retractable gripping and releasing mechanism, generally indicated at 14, on the distal end thereof and a moving handpiece assembly, generally indicated at 16, on the proximal end thereof. The moving assembly 16 is manually operable to expand and retract the gripping an releasing mechanism 14. As shown, the cannula assembly 12 of the medical extractor 10 is capable of being inserted through the central passage of a conventional scope deployed with a patient with the gripping and releasing mechanism 14 extending within the patient outwardly of the distal end of the scope and the moving assembly 16 disposed inwardly of the proximate end of the scope exteriorly of the patient. The construction of the extractor 10, as shown, can be made to pass through the central passage of a scope which measures three French.

The cannula assembly 12 and the gripping and releasing mechanism 14 constitute a subassembly of he extractor 10 which is preferably made in accordance with a method embodying the principles of the present invention. The starting materials used in practicing the method of the present invention to make the gripping and releasing mechanism 14 include (1) a series (three) of elongated flexible wire receiving tubular structures 18 and (2) a corresponding number of wires, generally indicated at 20. Each wire 20 includes a relatively long movable wire section 22 and a relatively short fixed wire section 24 integrally connected with one end of the movable wire section 22 by a kink 26. The starting materials also include (3) a corresponding number of tubular elements 28 of thermoplastic material; and (4) A corresponding number of heat shrinkable sleeves 30.

Figure 3:
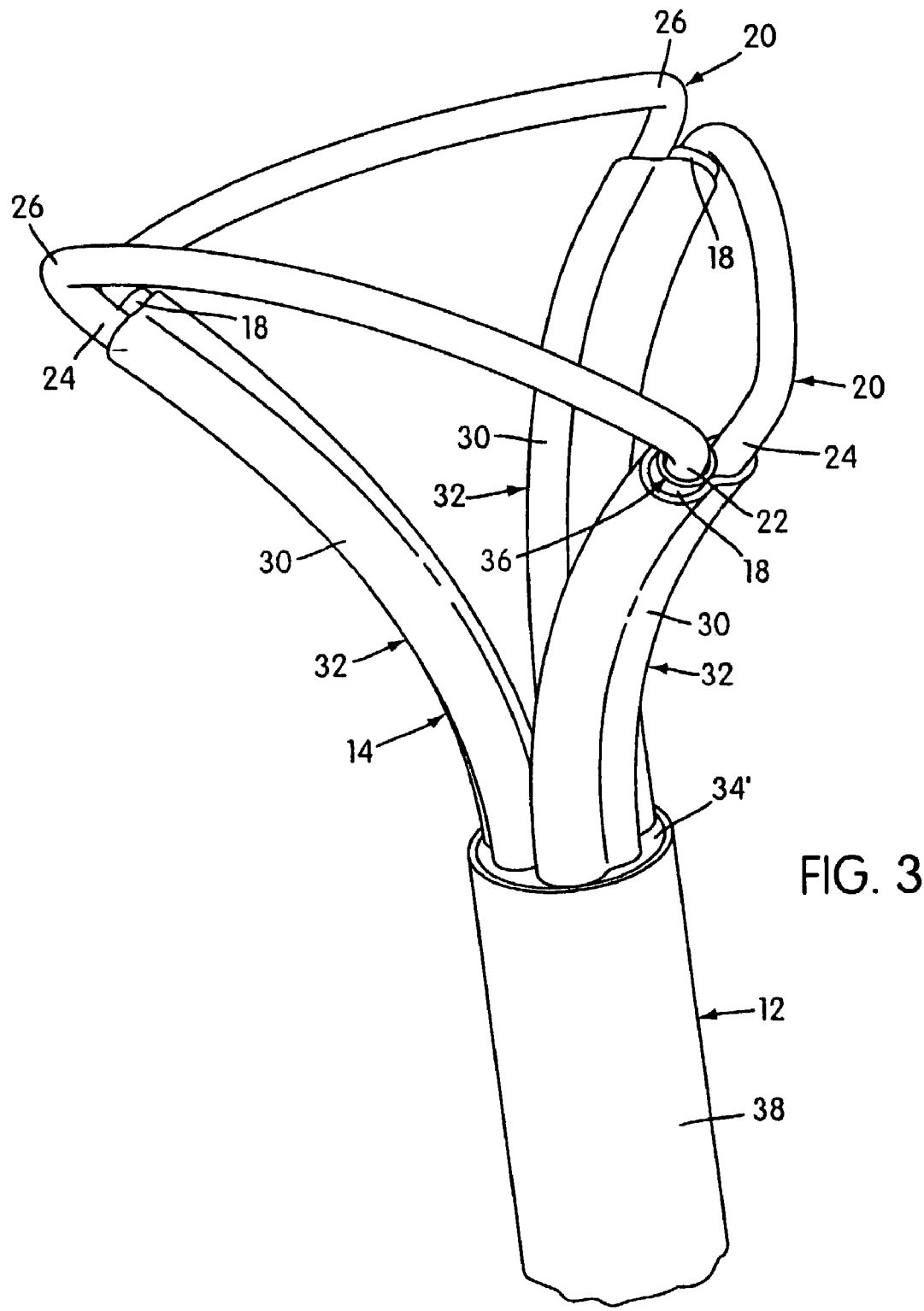
FIG. 3 is a view similar to FIG. 1 showing the parts in an open position.
Figure 5:
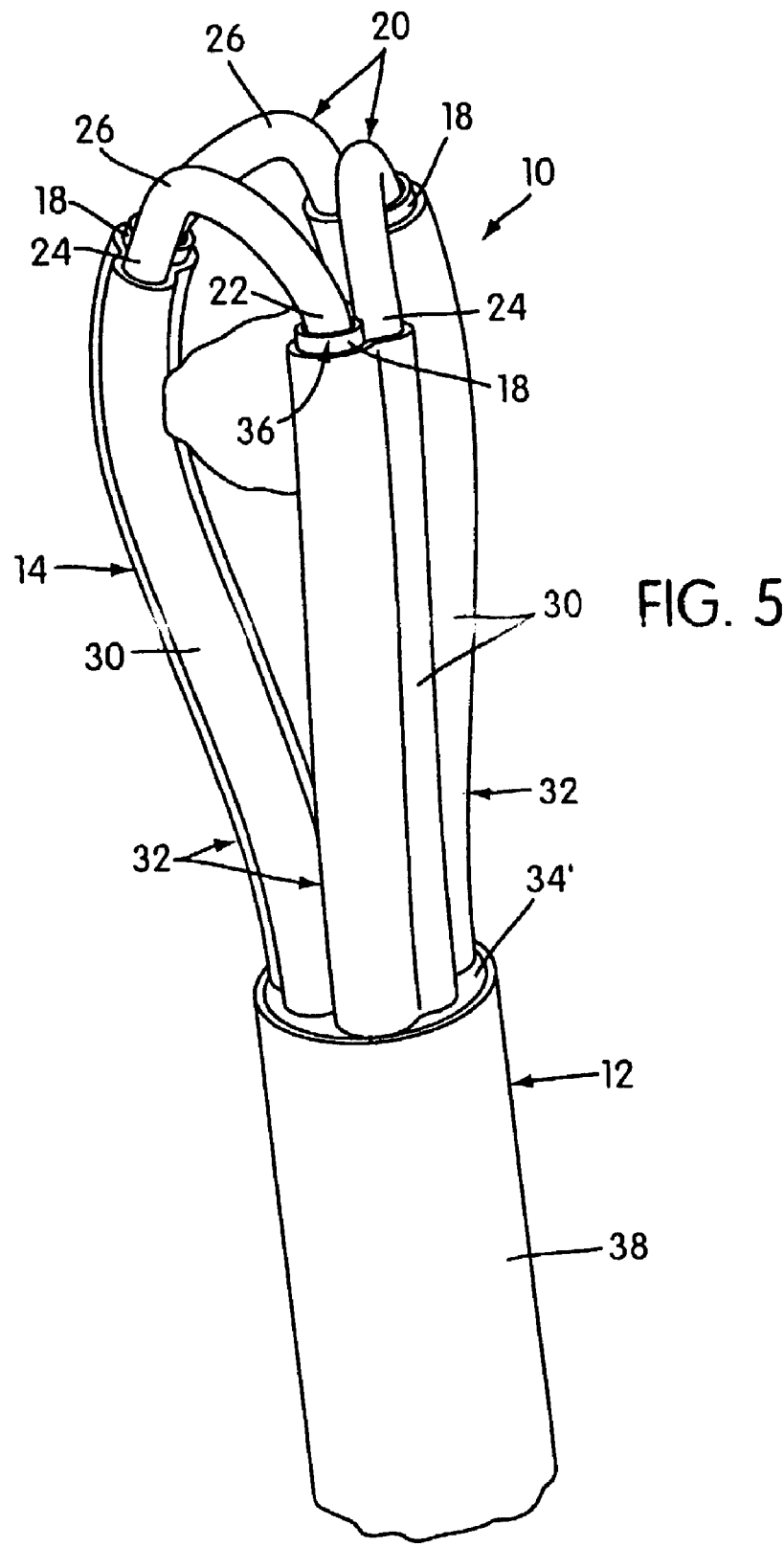
FIG. 5 is a view similar to FIGS. 1 and 3 showing the parts in a stone gripping position.
Figure 6:
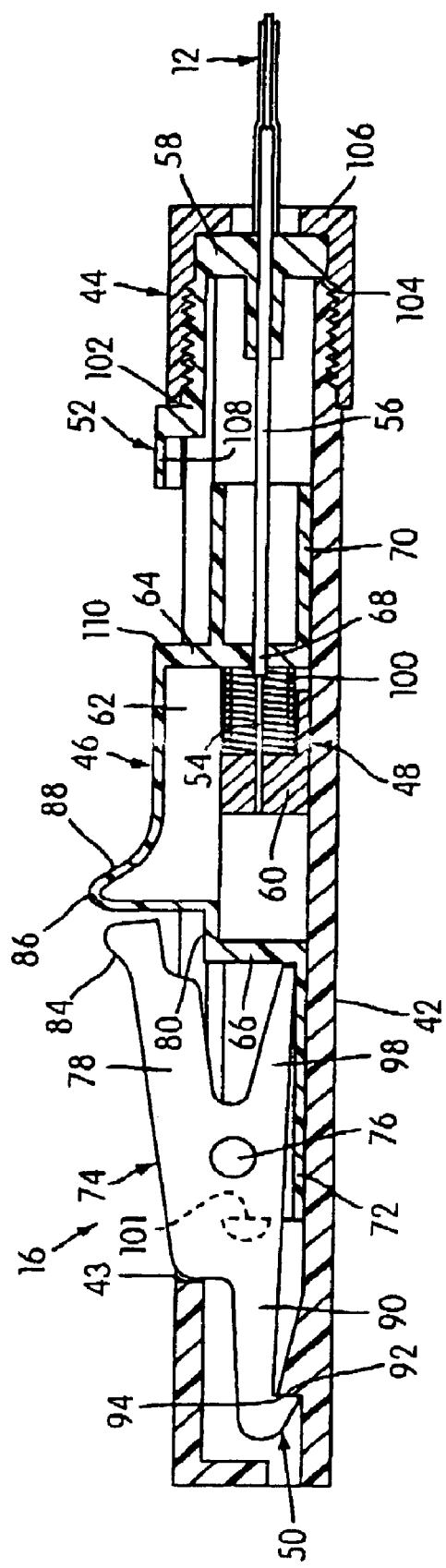
FIG. 6 is a view similar to FIGS. 2 and 4 showing the parts in a stone gripping position corresponding to the position of the parts in FIG. 5.
Figure 7:
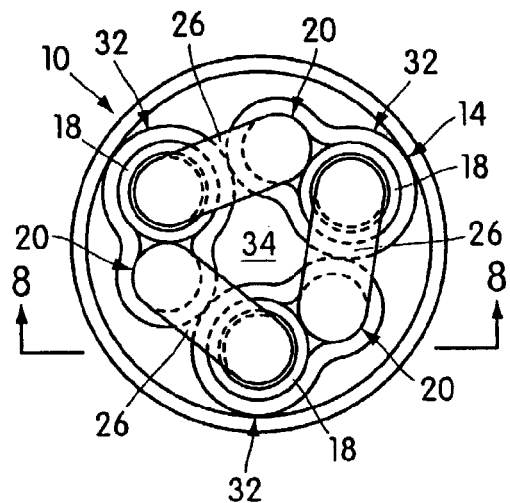
FIG. 7 is an enlarged top plan view of the gripping and releasing mechanism of tthe present invention showing the same in a closed position.

The tubular structures 18 shown in FIGS 1, 3 and 5 are tubes made of a flexible, thin walled plastic material capable of stably withstanding relatively high temperatures and of resisting longitudinal stretch. The tubular structures 18 are sized to provide an interior diameter to slidably receive and closely confine an associated movable wire section 22 therein. A preferred example of a material which can be utilized to form the wire receiving tubular structures 18 is polymide having a wall thickness of 0.0005". Another exemplary material is (PEEK) Polyethyl ethyl keystone.

The wires 20 are preferably made of a kink resistant metal, preferably a shape memory metal such as nitinol. Preferably, the kink 26 is formed in memory as an acute included angle between the fixed and movable wire sections 20 and 22 which extend co-extensively rom the kink 26. A preferred range being 80° to 45° with 50° being a preferred angle. An exemplary dimension for the nitinol wires is with the range 0.007" to 0.0085".

Figure 9:
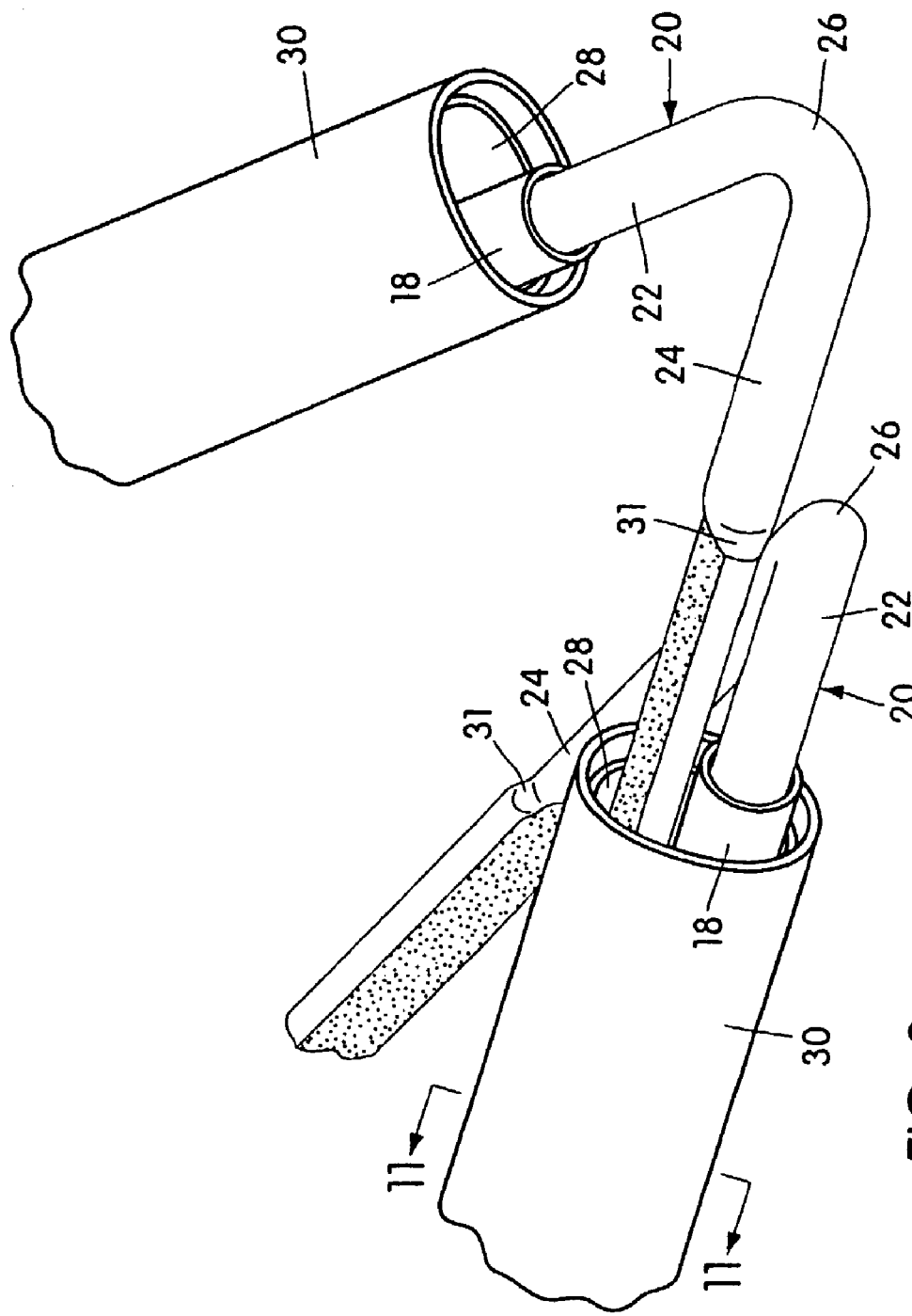
FIG. 9 is a perspective view illusrating an initial step in the sassembly of he gripping and releasing mechanism according to the method of the present invention.
Figure 10:
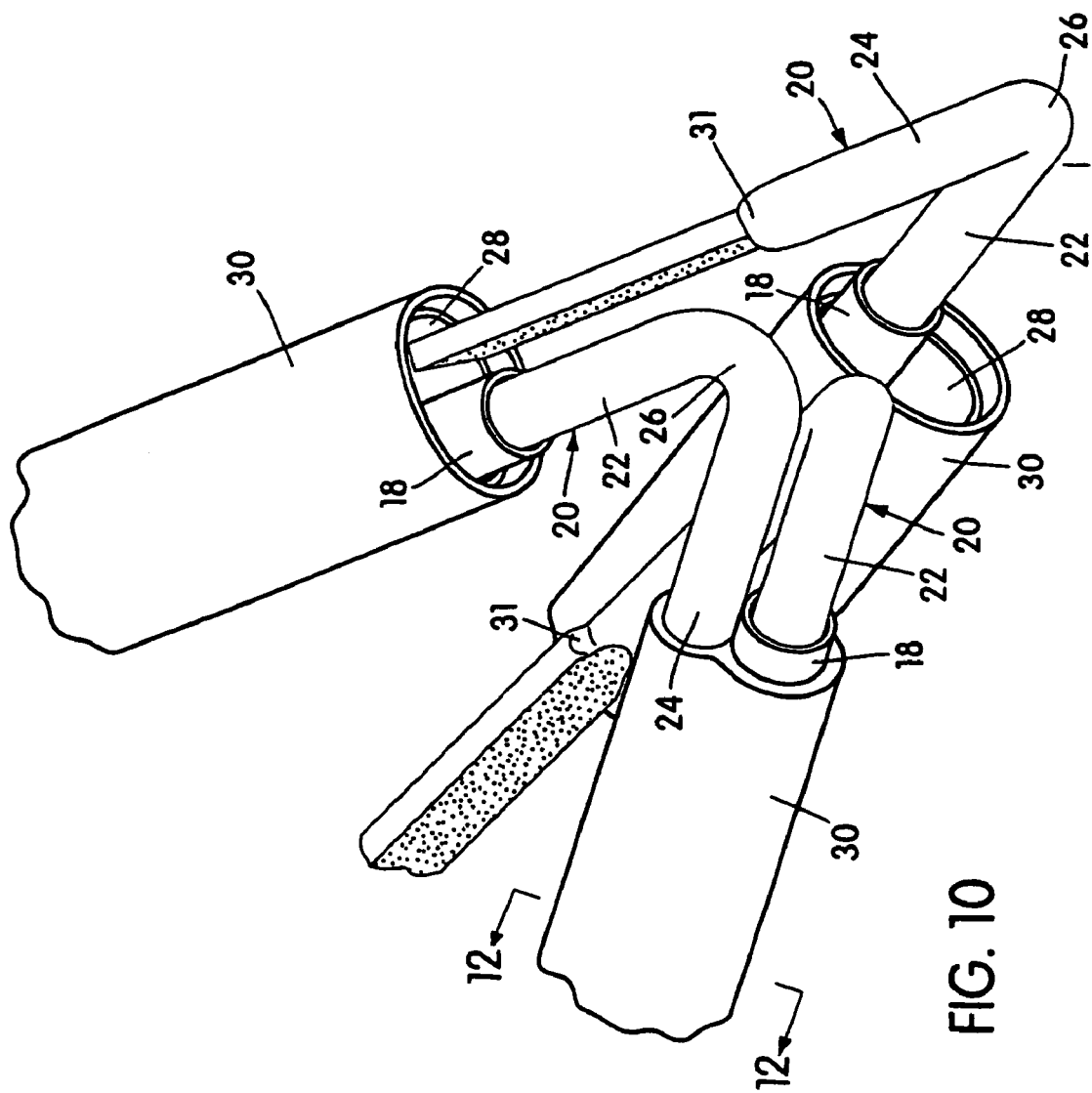
FIG. 10 is a view similar to FIG. 9 illustrating a subsequent step in the assembly.
Figure 11:
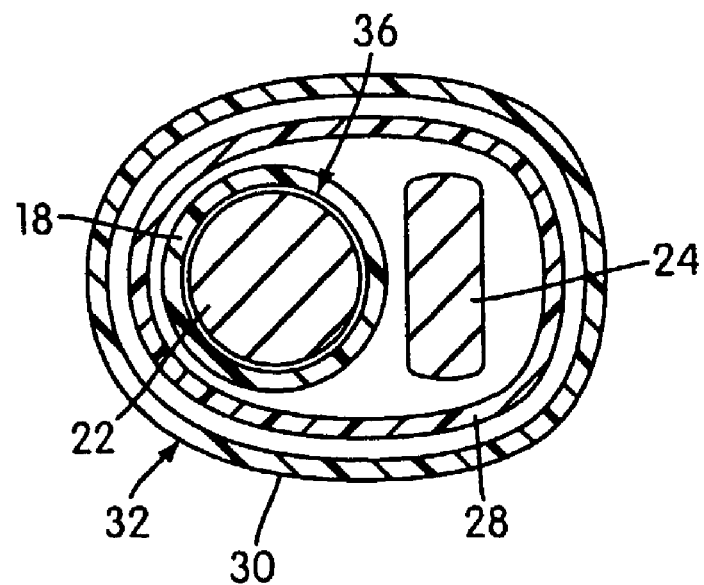
FIG. 11 is a sectional view taken along the line 11—11 of FIG. 9.

As best shown in FIGS. 9 and 10, preferably, the fixed wire section 24 of each wire 20 has a free end portion thereof flattened, as by a squeezing action between two rollers, so as to provide a pair of spaced shoulders 31 facing toward the associated king 26. Preferably, the opposed exterior surfaces of each flattened portion are abraded, as indicated by the stippling in FIGS. 9 and 20, to enhance the adherence thereof to the thermoplastic material of the associated tubular element 28.

Figure 12:
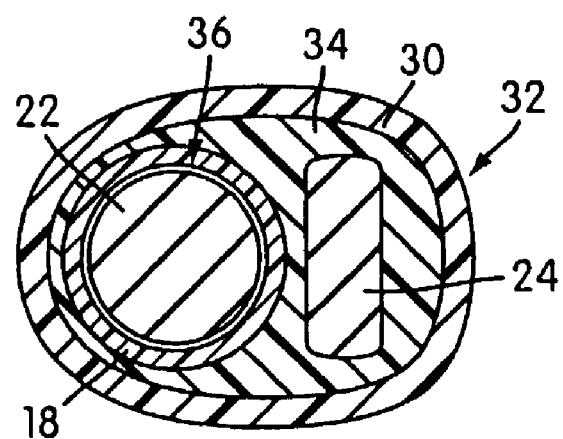
FIG. 12 is a sectional view taken along the line 12—12 of FIG. 10.

The tubular elements 28 are shown in FIGS. 9, 10 and 12. A preferred material is high density polyethylene. The interior diameter size of the surrounding tubular elements 28 are oversize with respect to exterior diameter size of the wire receiving tubular structures 18. The length of the tubular elements 28 is slightly in excess of the length of the heat shrinkable sleeves 30, e.g. ¼ inch.

Each heat shrinkable sleeve 30 is preferably somewhat oversize in diameter with respect to the tubular elements 28 and is formed of a material having a relatively high shrink temperature. A preferred material is PET—polyester resin, although other suitable materials may be utilized.

Ultimately, the kinked wires 20, the distal end portions of the wire receiving tubular structures 18, the surrounding tubular elements 28, nd the heat shrinkable sleeves 30 are assembled so as to form the gripping and releasing mechanism 14. In the assembly, a movable wire section 22 is disposed within each flexible tube 30 and a distal end portion of each flexible tubular structure 18 is assembled together with a fixed wire section 24, a tubular element 28, and a heat shrinkable sleeve 30 so that (1) the fixed wire section 24 extends along the exterior periphery of the flexible tubular structure 18 with the kink 26 disposed outwardly of the distal end thereof, (2) the tubular element 28 is disposed in surrounding relation to the fixed wire section 24 and the flexible tubular structure 18 and (3) the heat shrinkable sleeve 30 is disposed in surrounding relation to the tubular element 28 so that a short proximal end portion of the tubular element 28 (e.g. ¼ inch) extends beyond the proximal end of the heat shrinkable sleeve 30. It is noted that the surrounding position of the tubular element 28 with respect to the fixed wire section 24 insures that the shoulders 31 of the flattened free ends of the fixed wire sections 24 are covered by thermoplastic *material*.

Preferably, as shown in FIG. 10, each flexible tubular structure 18 is assembled with a fixed wire section 14, a tubular element 28 and a heat shrinkable sleeve 30 in the positions indicated, heat is applied progressively to the exterior of the heat shrinkable sleeve 30 of the assembly at a temperature and for a time sufficient to cause the hat shrinkable sleeve 30 to shrink or contract around the coextensive portion of the associated surrounding tubular element 28. The heat preferably is applied by a hot air blast at a temperature which will soften the thermoplastic material of the coextensive portion of the surround tubular element 28 causing it to flow into adhered contact with the exterior peripheries of the fixed wire section 24 and the distal end portion of the tubular structure 18. Once the heat is removed and the components are allowed to cool, the thermoplastic material of the coextensive portions of the surround tubular elements 28 serves to adhere each fixed wire section 24 to the exterior periphery of the distal end portion of the associated wire receiving tubular structure 18.

The sequential heating of each heat shrinkable sleeve 30 as it is assembled, as shown in FIGS. 9 and 10, is, as aforesaid, preferred because only one assembly need be maintained in potion at one time and then fixed in that position by the application of hat. However, it is within the broadest aspects of the present invention to complete all three assemblies and then effect the heating.

Figure 8:
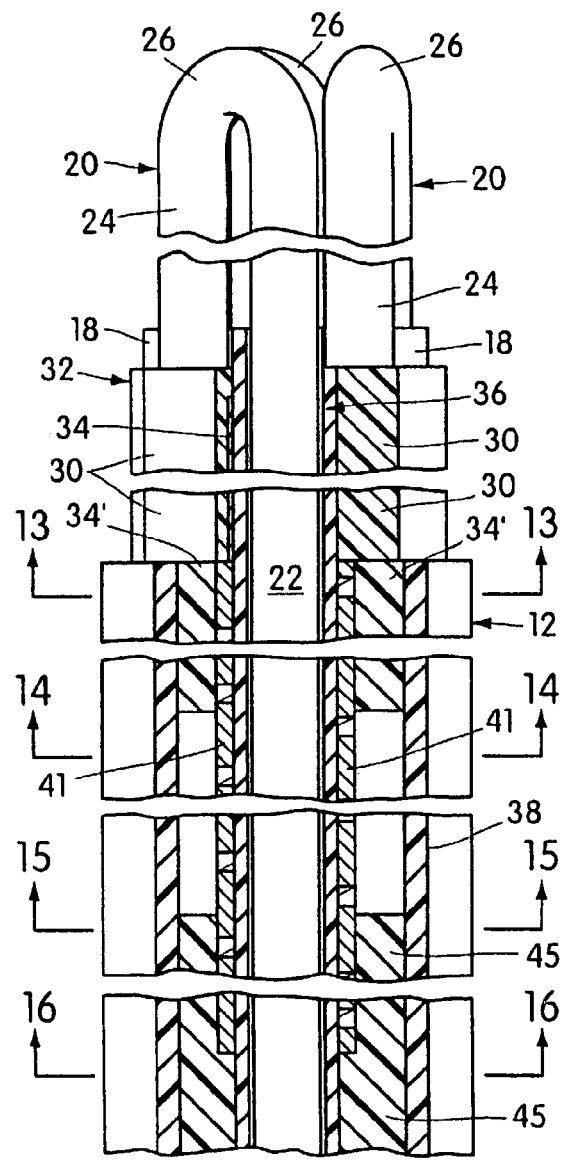
FIG. 8 is a fragmentary sectional view taken along the line 8—8 of FIG. 7.

In this way, there are formed at the distal end of the cannula assemle 13 three flexure elements 32, each of which, as shown in FIG. 8, is comprised of the coextensive distal end portion of the associated wire receiving tubular structure 18, a fixed wire section 24, a surrounding body of molded thermoplastic material indicated at 34 in FIG. 8 and a coextensive surrounding short heat shrinkable sleeve 30 in a heat contracted condition defining the exterior molded shape of the body of thermoplastic material 34. The three flexure elements 32 are fixed together at their proximal ends in a manner hereinafter to be described so as to constitute fixed flexure elements 32 of he gripping and releasing mechanism 14. The distal portions of the movable wire sections 22 which move out of and are slidable within the fixed flexure elements 32 constitute movable flexure elements 36 of the gripping and releasing mechanism 14.

The fixing of the proximal ends of the fixed flexure elements 32 is preferably accomplished in conjunction with the assembly and making of the cannula assembly 12.

The subassembly resulting from the above procedures includes parts of the cannula assembly 12 with the gripping and releasing mechanism 14 connected at its distal end. The fixed and movable flexure elements 32 and 36 constitute fixed and movable parts of the gripping and releasing mechanism 14. The main extent of the wire receiving tubular structures 18 ar next contained together in coextensive relation to form the fixed structure of the cannula assembly 12 while the main extend of the movable wire sections 22 constitute the movable sructure of the cannula assembly 12. Thus, the connections of both the fixed structure or parts and the movable structure or parts between the distal end of the cannula assembly 12 and gripping and releasing mechanism 14 are essentially automatically made integral connections in that the portions of the flexible tubular structures 18 of the cannula assembly 12 form extensions of the distal portions forming the fixed flexure element 32 of the gripping and releasing mechanism 14 and the main portions of the movable wire sections 24 form extensions of the distal portions forming the movable flexure elements 36 of the gripping and releasing mechanism 14.

Figure 16:
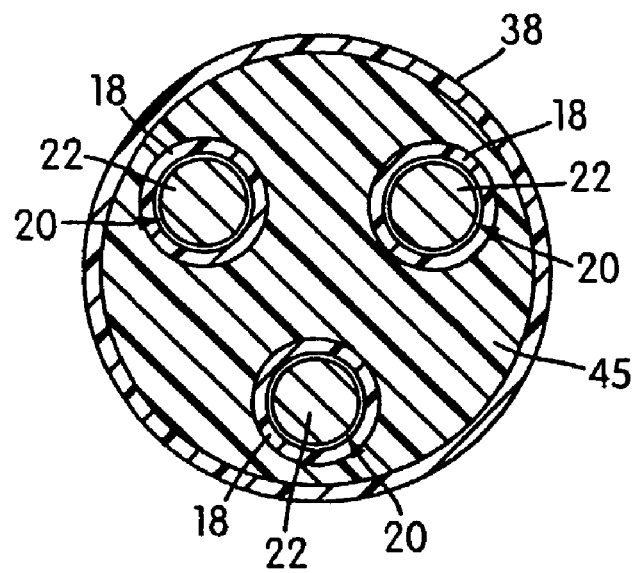
FIG. 16 is a cross-sectional view aken along the line 16—16 of FIG. 8.
Figure 17:
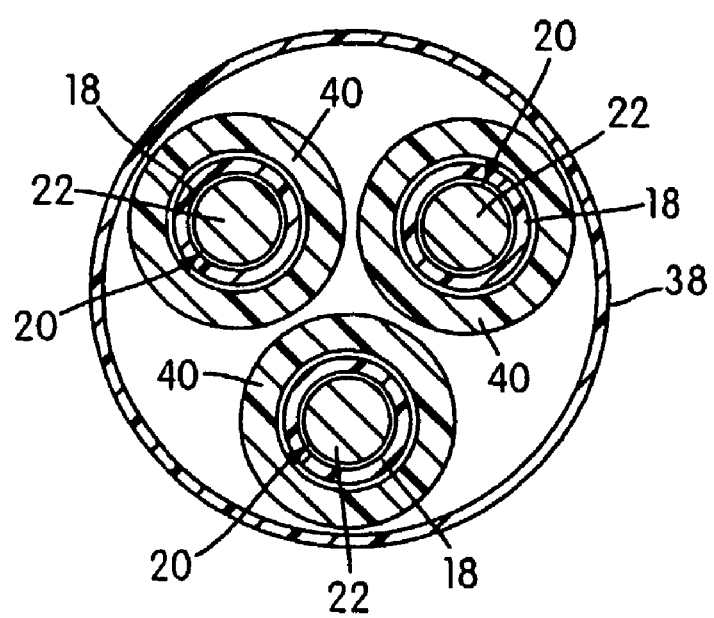
FIG. 17 is a cross-sectional view taken along the line 16—16 of FIG. 8 showing the position of the parts in an initial assembly condition.
Figure 18:
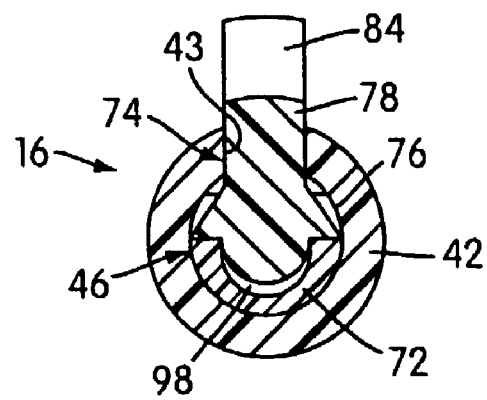
FIG. 18 is a cross-sectional view taken along the line 18—18 of FIG. 8.
Figure 19:
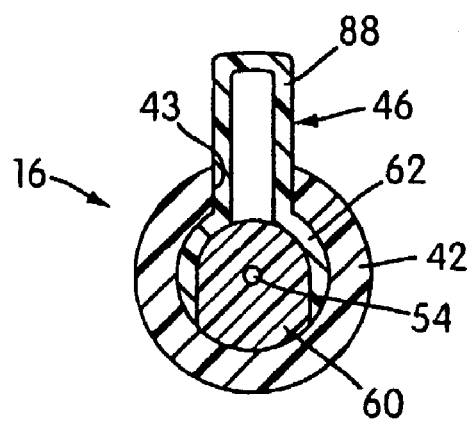
FIG. 19 is a sectional view taken along the line 19—19 of FIG. 2.
Figure 20:
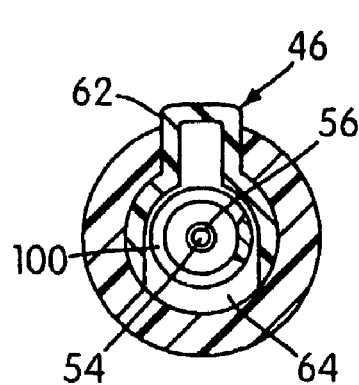
FIG. 20 is a sectional view taken along the line 20—20 of FIG. 2.
Figure 21:
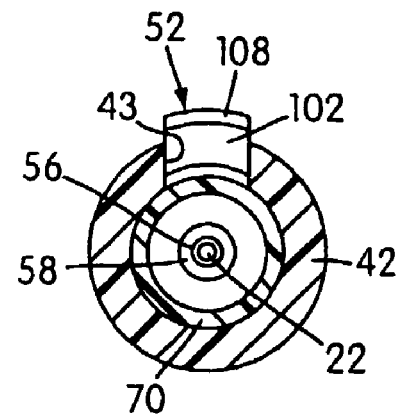
FIG. 21 is a sectional view taken along the line 21—21 of FIG. 2.

As best shown in FIGS. 8, 16 and 17, the containing procedure involves the use of an elongated heat shrinkable outer sleeve 38 of a length sufficient to extend throughout the cannula assembly 11 and a series of elongated tubular elements 40 of a somewhat lesser length, as for example, approximately four inches less. The outer sleeve 38 is preferably formed of irradiated cross linked polyethylene and the tubular elements 40 are preferable of high density polyethylene.

Each tubular element 40 of the series is positioned over a main proximal end portion of one of the tube extensions 18 and the outer sleeve 38 is positioned over the tubular elements 40 and the remaining uncovered distal sections of the tube extensions 18. These distal sections of the tube extensions 18 provide a distal section of the cannula assembly 12 which is more flexible than the remainder. This flexibility characteristics is valuable when the medical device 10 is used to extract stones in the kidneys.

As best shown in FIG. 8, the distal section of each tube extension 18 has mounted n the exterior periphery thereof a collapse preventing structure in the form of a coil of metal 41. While the metal may be wire, a preferred form is a ribbon (e.g..001"×.003") of stainless steel coiled with successive loops spaced slightly apart with the larger dimension disposed axially. Collapse prevention is desirable as this section of the cannula assembly 12 must undergo a somewhat severe 180° curvature when the device 10 is used to extract a kidney stone.

As previously indicated, the fixing of the fixed flexure elements 32 is preferably accomplished in conjunction with the assembly of the cannula assembly 12. The fixing procedure involves moving the proximal end portions of the tubular elements 28 extending from the sleeves 30 together and then surrounding the same with a distal end portion of the outer heat shrinkable sleeve 38.

It is now possible to effect a controlled progressive heating of the exterior periphery of the elongated heat shrinkable outer sleeve 38 starting at its distal nd so that the distal end portion is first made to shrink and mold the thermoplastic material of the extensions of the tubular elements 28 into engaged relation to the exterior peripheries of the coextensive lengths of the wire receiving tubular structures 18.

The progressive heating of the next four inches of the elongated hat shrinkable sleeve 38 is such as to make the elongated heat shrinkable outer sleeve 38 to shrink but only to an extent sufficient to confine and contain the surrounded portions of the wire receiving tubular structures 18 and surround coils 41.

The progressive heating of the remainder of the elongated heat shrinkable outer sleeve 38 is accomplished at a temperature sufficient to shrink the elongated heat shrinkable outer sleeve 38 and soften and mold the thermoplastic material of the surrounded tubular elements 40 into adhered relation to the surrounded exterior peripheries of the wire receiving tubular structures 18.

In accordance with one feature of the present invention, the fixed flexure elements 32 are self-biased to move into the opened condition thereof by an appropriate heat treatment while held in a position preferably beyond the normal opened position. The term self-biased means biased by the materials which make up the fixed flexure elements 32.

A typical heat treatment involves first extending the movable wire sections 22 outwardly to maintain the fixed flexure elements 32 in the extended open position thereof and maintaining it there at a temperature below the melting point of the thermoplastic material of the tubular elements 28 for a time period sufficient to impart a bias to the fixed flexure elements 32 to move into the open position thereof. An exemplary time is approximately twenty minutes and an exemplary temperature is approximately 230° F.

It is noted that at the proximal end portion of the cannula assembly 12 of the subassembly, the three movable wire sections 22 extend outwardly of the proximal end of the wire receiving tubular structures 18 which are surrounded by a body of molded thermoplastic material 34. The proximal ends of the movable and fixed parts of the cannula assembly 12 are then connected to movable and fixed parts respectively of the moving assembly 16.

It is now possible to effect a controlled progressive heating of the exterior periphery of the elongated heat shrinkable outer sleeve 39 starting at its distal nd so that the distal end portion is first made to shrink and mold the thermoplastic material of the extensions of the tubular elements 28 into a molded body of thermoplastic material 34', adhered relation to the exterior peripheries of the coextensive lengths of the wire receiving tubes 18.

The progressive heating of the nest four inches of the elongated heat shrinkable tube 40 is such as to make the elongated heat shrinkable outer sleeve 39 to shrink but only to an extend sufficient to confine and contain the surrounded portions of the wire receiving tubes 18 and surrounding cores 41.

The progressive heating of the remainder of the elongated heat shrinkable outer sleeve 39 is accomplished at a temperature sufficient to shrink the elongated heat shrinkable outer sleeve 39 and mold the surrounded tubular elements 40, as a molded body 45 of thermoplastic material into adhered relation to the surrounded exterior peripheries of the wire receiving tubes 18.

The progressive heating of the next four inches of the elongated heat shrinkable tube 40 is such as to make the elongated heat shrinkable outer sleeve 39 to shrink but only to an extend sufficient to confine and contain the surrounded portions of the wire receiving tubes 18 and surround cores 41.

The progressive heating of the remainder of the elongated heat shrinkable outer sleeve 39 is accomplished at a temperature sufficient to shrink the elongated heat shrinkable outer sleeve 39 and mold the surrounded tubular elements 40, as a molded body 45 of thermoplastic material into adhered relation to the surrounded exterior peripheries of the wire receiving tubes 18.

In accordance with one feature of the present invention, the fixed flexure elements 32 are biased to move into the opened condition thereof by an appropriate heat treatment while held in a position preferably beyond the normal opened position.

It is noted that at the proximal end portion of the cannula assembly 12 of the subassembly, the three movable wire sections 22 extend outwardly of the proximal nd of the wire receiving tubes 18 which are surrounded by a body of molded thermoplastic material. The proximal ends of the movable and fixed parts respectively of the moving assembly 16.

While the moving assembly 16 may assume any know configuration, one embodiment of a moving assembly 16, constructed in accordance with the principles of the present invention, which may be utilized is shown in FIGS. 1, 3, 5 and 13–26. As shown, the fixed part or fixed sructure of the moving assembly 16 includes a cylindrical housing member 42 having a longitudinal slot 4 extending substantially therethrough from a distal or forward end thereof and a cap assembly generally indicated at 44, fixed at the distal end of the housing member 42 which serves to connect the fixed part of the moving assembly 16 with the fixed part of the proximal end of the cannula assembly 12. The movable part of the moving assembly 16 includes a slide structure, generally indicated at 46, mounted within the cylindrical housing member 42 for longitudinal sliding movement in opposite directions.

In accordance with the principles of the present invention, a motion transmitting mechanism, generally indicated at 48, serves to connect the moving parts of the moving assembly 16 and cannula assembly 12. In accordance with the principles of the present invention, the motion transmitting mechanism 48 is constructed and arranged to enable (1) a manual movement of the moving part of the moving assembly 16 in one direction through an opening stroke to effect movement of the movable part of the gripping and releasing mechanism 14 through an opening stroke into a stone receiving open position, and (2) a manual movement of the moving part of the moving assembly 16 in an opposite direction through a gripping stroke to effect movement of the movable part of the gripping and releasing mechanism 14 through a gripping stroke toward a closed limiting position to establish a gripping relation with a stone and (3) further a manual movement of the moving part of the moving assembly 16 toward the closed limiting position to effect the application of a limiting resiliently yielding force to the movable part of the gripping and releasing mechanism 14 to maintain the gripping relation with the stone.

In accordance with the principles of the present invention, the slide structure 46 includes a releasable locking mechanism, generally indicated at 50, which cooperates with structure of the housing member 42 to releasably lock the moving part of the moving assembly 16 against movement in the aforesaid one direction when the moving part has been moved a predetermined distance in the opposite direction beyond the gripping stroke to maintain the gripping relation by the applied limiting force without the necessity to maintain manual engagement of the moving part of the moving assembly 16.

Also in accordance with the principles of the present invention, the moving assembly 16 preferably includes a stop structure, generally indicated at 52, configured and positioned in a normal operating position to determine a normally operable opening limiting position for the moving part of the moving assembly 16. The stop structure 52 is operable to be moved out of the normal operation position thereof to enable the moving part of the moving assembly 16 to have an increased opening stroke under emergency conditions.

The connection between the movable parts of the moving assembly 16 and the cannula assembly 12 includes an elongated metal tube 54 of hypodermic needle stock which forms the proximal end of the movable part of the cannula assembly 12. As shown, the metal tube 54 preferably constitutes the inner tube of a pair of telescopic tubes which also includes an outer metal tube 56 forming the proximal end of the fixed part of the cannula assembly 12.

The inner metal tube 54 is configured to receive therein the outwardly extending proximal ends of the three movable wire sections 22 and to have the wire sections 22 fixedly secured with respect thereto. While the mode of securement could be by a mechanical fastener arrangement, a preferred mode is simply to allow a drop of a viscous adhesive to move within the tube 54 by capillary action into surround relation to the wire sections 22 therein so as to effect an adhesive fixed securement. The adhesive securement is preferably accomplished with the gripping and releasing mechanism 14 in the closed limiting position thereof and the inner metal tube 54 spaced from the proximal end of the fixed part of the cannula assembly 12 a distance determined by the increased operative stroke of the movable part of the moving assembly 16.

The connection between the fixed part of the moving assembly 16 and the fixed part of the cannula assembly 12 is accomplished after the aforesaid securement of the inner metal tube 54. Initially, the outer metal tube 56 is moved rearwardly over the proximal end of the fixed part of the cannula assembly 12. Preferably, the exterior surface of the outer metal tube 56, which exemplarily made of stainless steel, is sand blasted so that it will adhesively adhere to a heated plastic contacted therewith.

As best shown in FIGS. 1, 3 and 5, it is preferable that the outer metal tube 56 forms an insert in a molding operation which serves to form over a central portion of the outer metal tube 56 near its forward end a molded plastic body 58 constituting a part of the cap assembly 44.

The inner metal tube 54 is also preferably formed with a molded plastic body 60 of U-shaped cross-sectional configuration adhered to its rearward end which constitutes a part of the motion transmitting mechanism 48.

Figure 14:
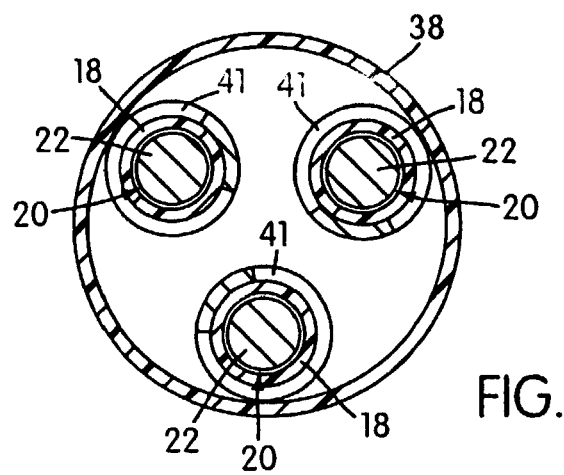
FIG. 14 is a cross-sectional view taken along the line 14—14 of FIG. 8.
Figure 15:
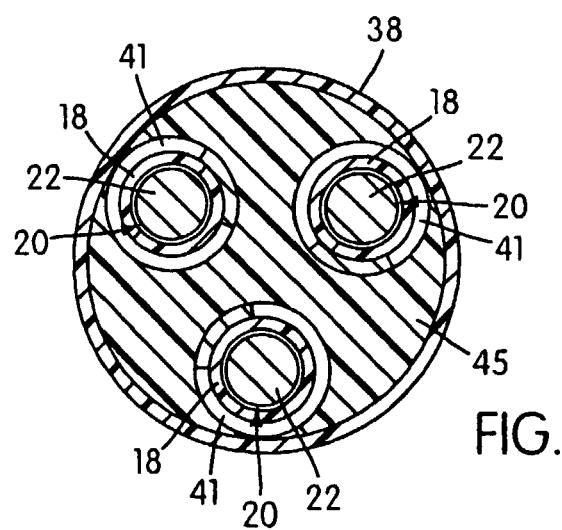
FIG. 15 is a cross-sectional view taken along the line 15—15 of FIG. 8.

The slide structure 46 includes a central section 62 of generally inverted U-shaped cross-sectional configuration as best shown in FIGS. 14 and 15, with the legs of the U having exterior arcuate surfaces to conform with the interior cylindrical surface of the slotted cylindrical housing member 42. The opposite ends of the central slide section 652 are integrally formed with forward and rearward end walls 64 and 66 respectively. The forward end wall 64 is centrally apertured to provide an opening 68 configured and positioned to slidably support the outer metal tube 56 therein.

The slide structure 46 includes a forward section 70 which extends forwardly of the forward end wall 64. The forward slide section 68 is of cylindrical configuration having an exterior periphery which slidably cooperates with the cylindrical interior periphery of the slotted cylindrical housing member 42.

The slide structure 46 also includes a rearward section 72 which includes a part of the releasable locking mechanism 50. As best shown in FIGS. 1, 3, 5 and 13, the releasable locking mechanism 50, like the sections 62, 64 and 66 of the slide structure 46 is formed as a molded plastic part. The slide structure 46 including the part of the releasable locking mechanism 50 forms a two-piece molded structure. It is within the broadest aspects of the present invention to make this two-piece structure as one molded part.

Figure 13:
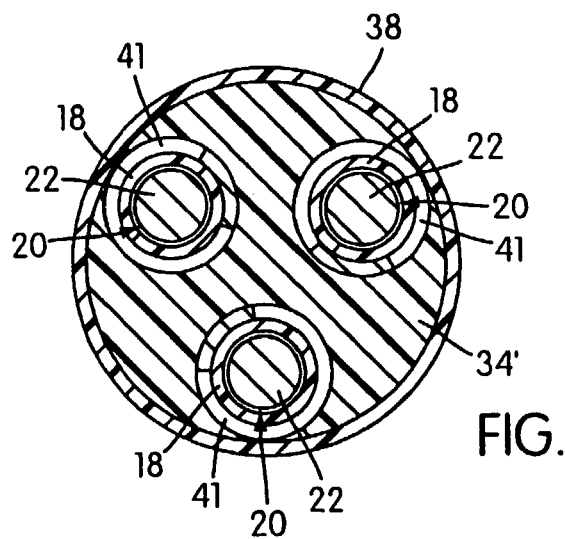

As shown in FIG. 13, the rearward slide section 72 is of U-shaped cross-sectional configuration an the associated part of the releasable locking mechanism 50 is in the form of a lever member generally indicated at 74. The lever member 74 is pivotally connected with the rearward slide section 72 as by a pair of integral stub shaft elements 76 which snap into receiving openings formed in the central upper portion of the rearward slide section 72.

The lever member 74 includes a digitally engageable arm portion 78 extending forwardly and upwardly from the central transverse pivotal axis of the lever member 74 provided by the stub shaft elements 76. The forward free end of the digitally engageable arm portion 78 extends upwardly through the slot A of the housing member 42 and overlies a lodge formation 80 integrally molded in the upper rearward portion of the central slide section 62. The free end of the arm portion 72 includes upwardly and rearwardly facing thumb engaging surface 84 for moving the lever member 74 in a clockwise direction, as viewed in FIGS. 1, 3 and 5, about its pivotal axis and the slide structure 46 forwardly within the housing member 42.

Formed integrally on the central slide section 62 forwardly of the ledge formation 80 is a digitally engageable hump shaped portion 86 extending upwardly through the slit 43 of the housing member 42. The hump portion 86 provides an upwardly and forwardly facing thumb engaging surface 88 for moving the slide structure rearwardly within the housing member 42.

The lever member 74 includes an integrally rearwardly extending arm portion 90 having a forwardly facing locking surface 92 for releasably engaging a rearwardly facing locking surface 97 of a ramp element 96 formed integrally on the interior periphery of the housing member 42 as a part of the releasable locking mechanism 50. The lever member 74 is based to move into a locking position wherein the locking surfaces 92 and 94 are engaged by a spring arm 98 formed integrally thereon and extending forwardly and downwardly from the pivotal axis. A free end of the spring arm 98 engages the central portion of the U-shaped section of the rearward slide section and slides therealong as the spring arm 98 flexes during the pivotal movement of the lever member 74 between the locking position and a releasing position wherein the locking surfaces are disengaged. Instead of the integral spring arm 98, a separate metal spring could be used.

Figure 2:
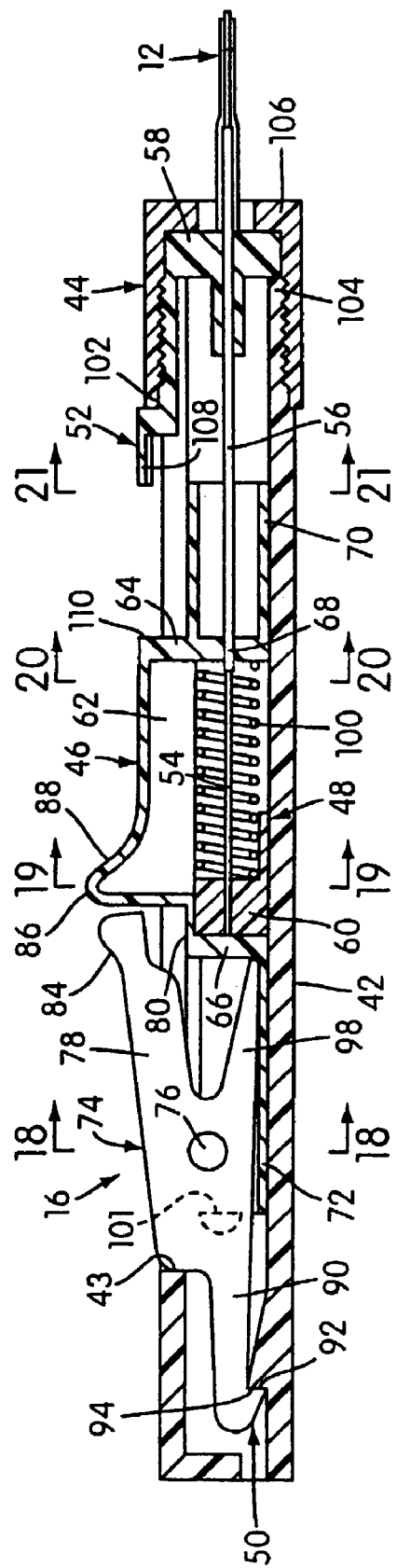
FIG. 2 is a cross-sectional view of a moving assembly and adjacent portion of the cannula assembly of the medical extractor showing the parts in a closed position corresponding to the position of the parts shown in FIG. 1.

The central slide section 62 forms a part of the motion transmitting mechanism 48 which also includes a compression coil spring 100. The coil spring 100 is initially assembled over the forward end of the inner metal tube 54 and then the forward end of the inner metal tube 54 is fed forwardly through the forward end wall opening 68 until the trailing surface of the u-shaped molded plastic body 60 on the inner metal tube 54 moves past the leading surface of the rearward end wall 66 and moves within the central slide section 62 into an operative position therein, as shown in FIGS. 2, 3 and 5. As can be seen in the operative position, he trailing surface of the plastic body 60 and the leading surface of the rearward end wall 66 are in abutting engagement and the coil spring 100 is compressed between the molded plastic body 58 and forward end wall 64.

The proximal ends of the movable wire sections 22 extending from the distal end of the fixed part of the cannula assembly 12 are then inserted within the forward end of the inner metal tube 54 so that a predetermined space is left between the forward end of the inner metal tube and the proximal end of the fixed part of the cannula assembly 12. The proximal ends of the movable wire sections are the fixed within the inner metal tube 54 by any suitable means, as for example, a drop of viscous adhesive can be fed to the forward end of the inner metal tube 54 and allowed to wick therein by capillary action and then allowed to cure or set. Epoxy is an exemplary adhesive.

Figure 4:
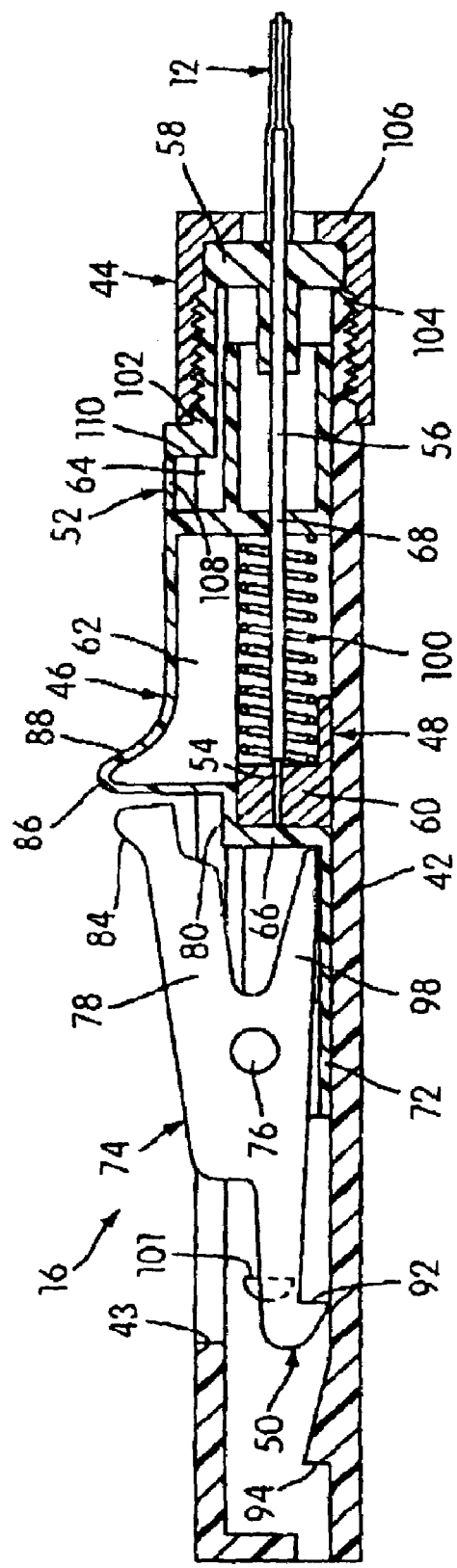
FIG. 4 is a view similar to FIG. 2 showing the parts in an open position corresponding to the position of the parts shown in FIG. 3.

After the inner metal tube 54 has been assembled in the slide structure 46 and adhered to the proximal ends of the movable wire sections 22, the outer metal tube 56 with its molded plastic body 58 is moved over the cannula assembly 12 into telescoping relation to the inner metal tube 54. Here again, a drop of viscous adhesive, such as epoxy, serves to fix the outer metal tube 56 to the cannula assembly 12 in predetermined spaced relationship equal to the aforesaid increased opening stroke. This completes a subassembly wherein the lever member 74 is pivoted to the rearward slide section 72 which may be accomplished as a last step or before. The subassembly is then fed axially into the forward open end of the slotted cylindrical housing member 42 until a rearwardly facing end surface of the slide section 72 engages a forwardly facing stop surface 101 formed in the housing member 42, as shown in FIG. 4.

The molded plastic body 58 includes a projecting slot entering portion 102 which enters the forward end of the slot 43 in engaged relation to the slot defining surfaces as the axial movement of the subassembly proceeds. The molded plastic body 58 also includes a rearwardly facing arcuately shaped flat surface 104 which engages the forward end surface of the housing member 42 when the subassembly reaches its operative position. Next, a cap member 106 forming a part of the cap assembly 44 is fed axially over the cannula assembly 12 and into operative position. In its operative position, the cap member 106 abuttingly engages the molded plastic body and is fixed to the forward exterior periphery of the slotted housing member 42. The securement as shown is a threaded securement although a snap action or glued securement could be utilized.

It will be noted that the stop structure 52 includes a thin arcuate stop element 108 extending rearwardly from the slot entering portion 1092 in a position to b engaged by a forwardly facing surface 110 of the slide structure 46 forming another part of the stop structure 52. The axial position of the stop element 108 determines the normal opening stroke and its length determines the increased opening stroke. It is noted that the arcuate thin configuration of the stop element 108 enables it to be easily cut off by a scalpel or scissors when necessary.

OPERATION

As previously indicated, the medical device 10 is made to cooperate with a scope. When used as a kidney stone extractor, typically, the scope will be entered into the kidney through the urinary canal. The medical device 10 with the gripping and releasing mechanism 14 and moving assembly 16 in the closed positions thereof, as shown in FIGS. 1 and 2, is fed through the central passageway of the scope. When the gripping and releasing mechanism 14 extends outwardly of the distal end of the passageway of the scope, the operator grasping the housing member 42 in one hand moves his thumb forwardly on the thumb engaging surface 84 of the digitally engageable arm position 82. Since the slide structure 46 is restrained against forward movement by the interengagement of locking surfaces 92 and 94, the arm portion 82 moves downwardly into engagement with the ledge formation 80 which effects a clockwise movement of the lever member 74 about its pivotal axis. The clockwise movement of the lever member 74 moves the stop surfaces 92 and 94 into a disengaged relationship and the spring arm 98 into a flexed or stressed relationship. With the stop surfaces 92 and 94 disengaged, the slide structure 46 can now move forwardly within the housing member 42 the thumb pushes forwardly. The forward movement of the rearward end wall 66 of the slide structure 46 by virtue of its abutting relationship with the rearwardly facing surface of the inner metal tube molded plastic body 60 moves the inner metal tube 54 forward in telescopic relation into the outer metal tube 56 which is fixed to the housing member 42 and to the fixed part of the cannula assembly 12. Since the movable wire sections 22 are fixed within the inner metal tube 54, they, in turn, are moved forwardly. Since each movable wire section 22 is contained throughout its length by a wire receiving tube 18, the distal end portions of the movable wire sections constituting the movable flexure elements 36 of the gripping and releasing mechanism 14 move outwardly of the distal ends of the wire receiving tubular structures 18. When the slide structure 46 has been moved from the closed limiting position thereof forwardly toward its opened limiting position through an operative opening stroke, as shown in FIG. 4, the gripping and releasing mechanism will have been moved toward the pen limiting position thereof into an expanded condition as defined by an annular series of transversely outwardly flexed fixed flexure elements 32 interconnected by an annular series of arcuately flexed portions of the movable flexure elements 36. The extent of the operative opening stroke is dependent upon the size of the stone to be extracted, but is normally limited by the engagement of the slide structure 46 with the stop surface 110 of the stop element 108, as shown in FIG. 4.

With the gripping and releasing mechanism 14 in its expanded condition, as shown in FIG. 3, the physician can then manipulate the open gripping and releasing mechanism 14 into surrounding relation to the stone within the kidney to be extracted. As soon as this stone surrounding relationship is established, the physician engages a thumb on the thumb engaging surface 88 of the hump shape portion 86 of the slide structure 46 to pull the slide structure 46 rearwardly with the housing member 42. The rearward movement of the slide structure 36 is transmitted to the inner metal tube 54 and hence movable wire sections 22 through the compressed coil spring 100 which is engaged between the forward end wall 64 and the inner tube molded plastic body 60. The rearward movement of the proximal end portions of the movable wire sections 22 with the inner metal tube 54 causes the movable flexure elements 32 to progressively retract the gripping and releasing mechanism 16 from its expanded condition into gripping relation to the stone, as shown in FIG. 5.

It will be noted that the strength of the coil spring is chosen so as to enable the physician to apply a digitized force in the gripping direction to effect an effective gripping relationship while limiting the transmission of an excessive digitized force to the movable wire sections 22 by yielding so as to allow continued rearward movement of the slide structure 46 unaccompanied by movement of the inner metal tube 54 and contained movable wire sections 22. The yielding force is chosen as one which can be readily applied so that a continuous rearward movement of the slide structure 46 will take place after the gripping stroke to move the slide structure 46 into its closed limiting position where the spring arm 98, stressed by the clockwise pivotal movement of the lever member 74 as the arm portion 90 rides up the ramp element 96, biases the lever member 74 to pivot in a counter clockwise direction as the arm portion 90 becomes free to move downwardly to engage locking surfaces 92 and 94. When the lever member 74 reaches this locking position, coil spring 100 has been compressed into a stressed condition transmitting a force to the inner metal tube and movable wire sections 22 which retains the movable flexure elements 36 of the gripping and releasing mechanism 16 in gripping relation to the stone. In this way, not only are the gripping forces which can be applied limited by a desirable gripping force releasably lockingly retained enabling the physician's hands to be released from the housing member 42 as the scope is withdrawn with the gripped stone in the gripping and releasing mechanism.

After withdrawal, the gripped stone can be released by simply digitally moving forwardly on the thumb engaging surface 84 to expand the gripping and releasing mechanism 14 and release the stone, after which the slide structure 46 can be returned to its closed limiting position.

When the gripping and releasing mechanism 14 is disposed in gripping engagement with a stone within the kidney and for some reason, it becomes desirable to release the stone and the operative opening stroke provided is insufficient to effect release, the physician can simply cut off the stop element 108 with a scalpel or scissors to provide an increased operative stroke which can be sufficient to effect release.

Referring now more particularly to FIGS. 22–27, there is shown therein a modified form of moving handpiece assembly, generally indicated at 128, which can be utilized in lieu of the moving handpiece assembly 16. The fixed part or fixed structure of the moving assembly 128 includes a pair of cooperating or mating housing half shell members 142. The part of shell members 142 when mated together provide rearward exterior surfaces 143 defining a hand grip section, a central upper slot 144, and a forward portion 145 which fixedly connects with a fixed part of the cannula assembly 12. The movable part of the moving assembly 128 includes a slide structure, generally indicated at 146 mounted within the mated housing shell members 142 for longitudinal sliding movement in opposite directions. The slide structure extends outwardly the mated housing shell members 142 through a slot 144' formed therein.

In accordance with the principles of the present invention, a motion transmitting mechanism, generally indicated at 148, serves to connect the moving parts of the moving assembly 128 and cannula assembly 12. In accordance with the principles of the present invention, the motion transmitting mechanism 148, as before with the motion transmitting mechanism 48, is constructed and arranged to enable (1) a manual movement of the moving part of the moving assembly 128 in an opposite direction through a gripping stroke to effect movement of the movable part of the gripping and releasing mechanism 14 through an opening stroke into a stone receiving open position, and (2) a manual movement of the moving part of the moving assembly 128 in an opposite direction through a gripping stroke to gripping stroke toward a closed limiting position to establish a gripping relation with a stone and (3) further a manual movement of the moving part of the moving assembly 128 toward the closed limiting position to effect the application of a limiting resiliently yielding force to the movable part of the gripping and releasing mechanism 14 to maintain the gripping relation with the stone.

In accordance with the principles of the present invention, the slide structure 146 includes a releasable locking mechanism, generally indicated at 150, which cooperates with structure of the mated housing shell members 142 to releasably lock the moving part of the moving assembly 128 against movement in the aforesaid one direction when the moving part has been moved a predetermined distance in the opposite direction beyond the gripping stroke to maintain the gripping relation by the applied limiting force without the necessity to maintain manual engagement of the moving part of the moving assembly 128.

Also in accordance with the principles of the present invention, the moving assembly 128 preferably includes a stop structure, generally indicated at 152, configured and positioned in a normal operating position to determine a normally operable opening limiting position for the moving part of the moving assembly 128. The stop structure 152 is operable to e moved out of the normal operation position thereof to enable the moving part of the moving assembly 128 to have an increased opening stroke under emergency conditions.

As before, the connection between the movable parts of the moving assembly 128 and the cannula assembly 12 includes an elongated metal tube 154 of hypodermic needle stock which forms the proximal end of the movable part of the cannula assembly 12. As shown, the metal tube 154 preferably constitutes the inner tube of a pair of telescopic tubes which also includes an outer metal tue 156 forming the proximal end of the fixed part of the cannula assembly 12.

The inner metal tube 154 is configured to receive therein the outwardly extending proximal ends of the three movable wire sections 22 and to have the wire sections 22 fixedly secured with respect thereto. While the mode of securement could be by a mechanical fastener arrangement, a preferred mode is simply to allow a drop of a viscous adhesive to move within the tube 154 by capillary action into surrounding relation to the wire sections 22 therein so as to effect an adhesive fixed securement. The adhesive securement is preferably accomplished with the gripping and releasing mechanism 14 in the closed limiting position thereof and the inner metal tube 154 spaced from the proximal end of the fixed part of the cannula assembly 12 a distance determined by the increased operative stroke of the movable part of the moving assembly 128.

The connection between the fixed parts of the moving assembly 128 and the cannula assembly 12 is accomplished after the aforesaid securement of the inner metal tube 154. Initially, the outer metal tube 156 is moved rearwardly over the proximal end of the fixed part of the cannula assembly 12.

As best shown in FIGS. 1, 3 and 5, it is preferable that the outer metal tube 156 is used an insert in a molding operation which serves to form over a portion of the outer metal tube 156 at its forward end a molded plastic body 158. A tube 159 is then preferably heat shrunk in a position to adhere to the exterior surface of the plastic body 158 and an adjacent exterior surface of the sleeve 40 defining the proximal fixed portion of cannula assembly 12.

The inner metal tube 154 is also preferably formed with a molded plastic body 160 of piston-like configuration adhered to its rearward end which constitutes a part of the motion transmitting mechanism 148.

Figure 26:
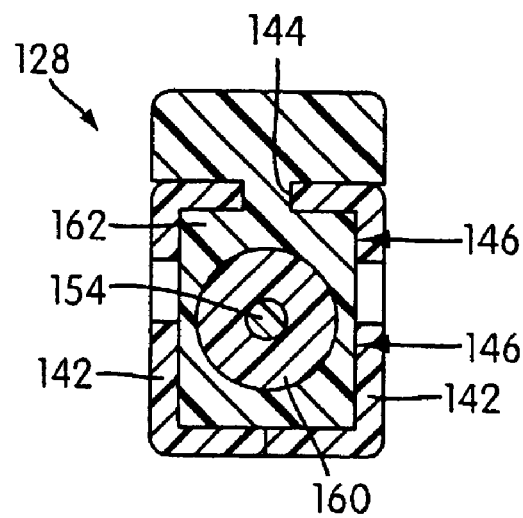
FIG. 26 is an enlarged sectional view taken along the line 16—26 of FIG. 22.
Figure 27:
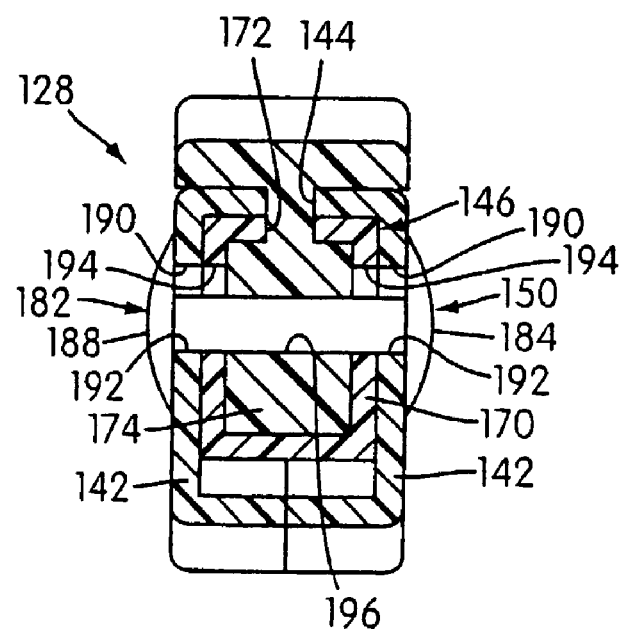
FIG. 27 is an enlarged sectional view taken along the line 27—27 of FIG. 22.

As best shown in FIGS. 26 and 27, the slide structure 146 includes a main central section 162 of generally rectangular exterior configuration to conform with the interior rectangular shaped surfaces of the housing shell members 142 when mated so as to enable the slide member 146 to be moved with a rectilinear movement forwardly and rearwardly therewithin. The slide member 146 opens forwardly from its rear end so as to form a forward cylindrical chamber 164 closed at its forward end by a forward end wall 166. The forward end wall 166 is centrally apertured to provide an opening 168 configured and positioned to slidably support the outer metal tube 156 therein.

The slide member 146 includes a rear section 170 having an upper slot 172 extending throughout the same and an interior configuration, which, as best shown in FIG. 27, is rectangular.

As best shown in FIGS. 22–24, the releasable locking mechanism 150 includes a pusher member 174, having a rectangular exterior configuration which slidably fits within the interior configuration of the rearward section 170 of the slide member 146 for movement therewith longitudinally and with respect thereto in forward and rearward directions.

It will be understood that slide member 146 is mounted in the position shown with respect to the outer metal tube 156 and piston body 160 prior to affixing the inner metal tube 154 to the proximal ends of the movable wire sections 22 as aforesaid. In addition, a coil spring 176 is initially fed over the outer metal tube 156 to engage rearwardly of the forward end wall 166 of the slide member 146. Coil spring 176 forms a part of the motion transmitting mechanism 148.

The pusher member 174 is slidable within the rearward section 170 from the rear. However, before effecting this connection, a second coil spring 177 is fed within the hollow rearward section 170 so as to engage at its forward end with the central section 162 of the slide member 146 and at its rearward end within forwardly facing recesses in the pusher member 174.

The pusher member 174 includes a digitally engageable portion 178 extending upwardly through the upper slot 172 and the slot 144 provided by the mating housing shell members 142.

Formed integrally on the central slide section 162 extending upwardly through the slot 144 provided by the mated housing shell members 142 is a digitally engageable puller portion 180. The puller portion 180 provides an upwardly and forwardly facing thumb engaging surface for moving the slide member 146 rearwardly within the mated housing shell members 142.

The releasable locking mechanism 150 also includes a locking element, generally indicated at 182, which, as shown, is in the form of a rivet or seprable two headed pin fastener. The locking element 182 includes a fixed head 184 formed on one end of a pin or shaft 186 and a second head 188 which is either after formed, as a conventional rivet head, or is capable of screwing into an internal thread to the opposite end of the pin 186.

The shaft 186 of the locking element 182 is arranged to extend through a pair of aligned longitudinally extending slots 190 having depending recesses 192 at their rear ends formed in the mating housing shell members 142, a pair of aligned vertically elongated openings 194 in the side walls of the rearward section 170 of the slide member 16 and a diagonal opening 196. The diagonal slot 196 could be straight, however as shown, it is of arcuate configuration defined on an upper side by a downwardly facing arcuate surface 198 and on a lower side by an upwardly facing arcuate surface 200.

The components of the motion transmitting mechanism 148 and the components of the releasable locking assembly 150 are assembled in the manner previously indicated and then mounted with respect to one of the housing shell members 142 having the locking element shaft 186 extending through the recess 192 of the slot 190 therein with the fixed head 184 in engagement with the adjacent exterior surfaces thereof. The mounting is accomplished by simply moving the components in the position shown in FIG. 22 laterally so that the locking element shaft 186 extends through the lower portion of the vertically elongated openings 194 in the slide member 146 and the forward end of the arcuate opening 196 in the pusher member 174. The other housing shell member 142 can then be moved into mating relation after which the second head 188 is added to the free end of the shaft 186. Finally, it is preferable that the two mated housing shell members 142 are heat fused together.

The moving handpiece assembly 128 is operated like the moving handpiece assembly 16 previously described except that the initial unlocking movement is accomplished by a rectilinear push forward of the pusher member 174 rather than a pivotal movement of the pivoted pusher member 74.

With respect to the locking action of the pusher member 174, it will be noted that the locking pin 186 is held within the recesses 192 of the slots 190 and the lower portion of the vertically elongated openings 194 by virtue of the engagement of the section of downwardly facing arcuate surface 198 at the forward end of the opening 196, which, in turn, is held in that position by the strength of coil spring 177 biasing the pusher member 274 rearwardly.

When the pusher member 174 is digitally moved forward by the operator's thumb pushing on pusher portion 178, the pusher member 174 is allowed to move forwardly by the compression of the coil spring 177. As the pusher member 174 moves forward, the upwardly facing arcuate surface 200 of the pusher member opening 196 engages the locking pin 186 and cams it upwardly so that it moves to the upper portion of the vertically elongated openings 194 and into alignment with the slots 190. When this condition is reached, as shown in FIG. 23, the surface defining end the reward end of the slot 196 of the pusher member 174 engages the pin 186 whose longitudinal movement results in a longitudinal movement of the slide member 146. In this position, it is preferable that the two thumb engaging portions 177 and 180 do not meet in such a way as to pinch the operator while it is desirable that the pusher almost engage if not engage the piston 160.

Once the pusher member 174 has reached this unlocked position shown in FIG. 23, continued forward movement will move the slide member 146 forward with respect to the mated housing shell members 142 and the inner metal tube 154 carrying the movable wire sections 22 forward with respect to the fixedly retained outer metal tube 156. It will be noted that when the operator releases the push on the pusher member 174, the coil spring 177 is ineffective to move the pusher member 174 rearwardly because the engagement of the locking pin 186 with the surfaces 200 defining the lower extent of the slot 194 prevents the upper arcuate surfaces 198 from camming the pin 186 downwardly. However, as soon as the slide member 146 is returned to its starting position and the locking pin 186 is moved in slot 190 over recess 192, coil spring 177 becomes effective to move the pusher member 174 rearwardly because arcuate surface 198 can now move the pin 186 downwardly into the recess 192.

Figure 28:
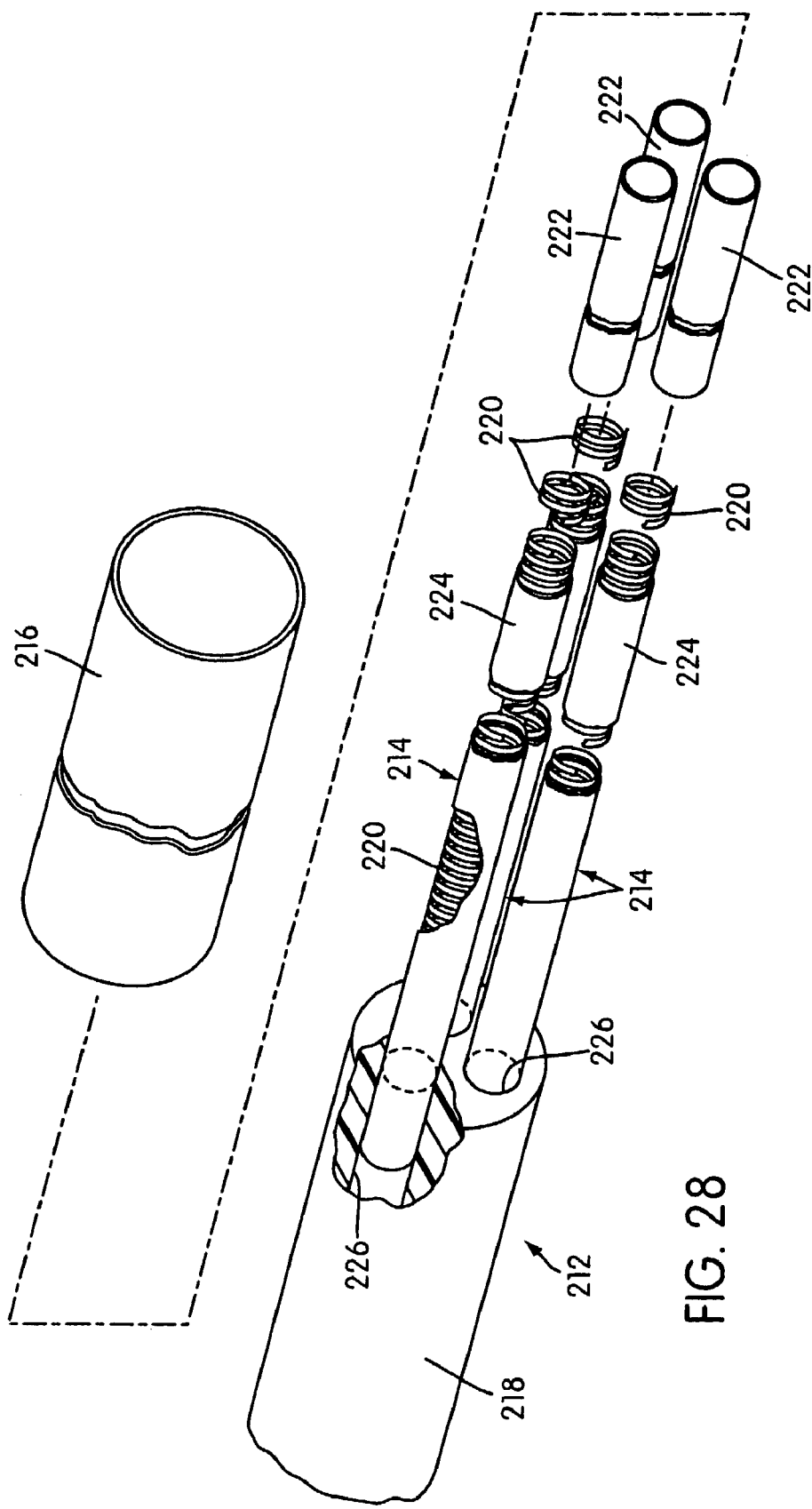
FIG. 28 is an exploded perspective view of replacement components useful in a modified form of device embodying he principles of the present invention.

Referring now more particularly to FIG. 28, there is shown thereon a modified wire receiving tubular assembly, generally indicated at 212, which can be utilized in lieu of the assemble provided by the series of tube 18, coils 41, tubular elements 40 and outer sleeve 39. The tubular assembly 212 includes a series of relatively short tubular structures 214 in the form of composite tubes (e.g. 4-½ inches), a slightly shorter heat shrinkable sleeve 216, preferably made of irradiate crosslinked *polyethylene*, and a relatively long three lumen extrusion structure 218 preferable made of PET.

Each tubular structure 214 is formed of a metal coil 220 of a construction similar to the coils 41 previously described. A short distal fixed flexure element defining portion of an coil 220 is covered with a heat shrinkable sleeve 222 preferably made of an elastomeric material as, for example, Pebax®. The remaining proximal portion of each coil 220 is coated, as indicated at 224, with a more longitudinally stable material, as, for example, polymide.

The coated proximal end portions of the coils 220 are inserted within distal end portions of lumens 226 formed in the extrusion 218 and then suitably secured therein as by gluing or otherwise.

Next, the elastomeric material covered distal end portions of the coils 120 are assembled with movable wire sections 22, flattened and abraded fixed wire sections 24, tubular elements 28 and heat shrinkable sleeve 30 in the manner previously described.

It will e noted that the lumens 226 of the extrusion structure 218 serve to contain and keep oriented the movable wire sections 22 while this assembly is carried out. The longitudinal extent of the coils 220 is sufficient to enable the person performing the assembly to effect the linear angular displacements of the distal wire ends necessary to complete the assembly.

After this assembly is completed, the formed flexure elements 32 are fixed together by first moving the extruded proximal end portions of the tubular elements 28 together and then extending (1) the distal end portion of the heat shrinkable sleeve 216 over the assembled tubular element end portions and (2) the proximal end portion of the heat shrinkable sleeve 216 over the distal end portion of the extrusion structure 218. Heat is then applied progressively to the exterior of the heat shrinkable sleeve 216 starting at the distal end portion thereof to shrink the same and mold the softened thermoplastic material of the tubular elements 28 into adhered relation to the exterior peripheries of the distal end portions of the coated portions of the coils 220. The heating progresses through the main central portion of the sleeve 216 so as to reduce it to confine the contained coated coils 220 but in an non-adhered relationship. The heating progresses finally to the proximal end portion of the sleeve 216 which is shrunk into adhered relation to the exterior surface of the extrusion structure 218.

The modification of FIG. 28 is simpler to assemble. The use of elastomeric material covered coils rather than tubes 18 as part of the fixed flexure elements 32 enables a greater amount of self bias to be imparted to the fixed flexure elements 32 during heat treatment since the covered coils 41 do not resist the bias to the same extent as the polymide polyethylene sleeve 216 and polymide coated sections of coils 220 provide a desired comparable longitudinal stability and lateral flexibility.

Referring now more particularly to FIG. 29, there is shown therein another modification of the fixed tubular structure of the cannula assembly 12 embodying the principles of the present invention. This modification involves substituting for the three lumen tubular member 218, a single lumen tubular member, generally indicated at 228. The single lumen tubular member is in the form of a composite laminate which includes a central reinforcing braid 230 sandwiched between inner and outer tubular layers 232 and 234 of a suitable plastic material.

An exemplary material for the braid 230 is stainless steel or Kevlar®. The plastic material of the layers 232 and 228 can be a wide variety of different materials, such as polyethylene, polyester, nylon, as preferred material being polytetraflouroethylene for its favorable low friction characteristics.

When the single lumen tubular member 228 is used, the integral extensions of the movable wire sections 22 are extended within the single lumen of the member in side by side relation. While this construction is within the contemplation of the invention, it is preferred to gather a main proximal portion of the side by side wire sections 22 into abutting relation and adhere them in abutting relation by heat shrinking a heat shrinkable sleeve or tube of a suitable plastic material. The sleeve begins at a distal point space in the proximal direction from the proximal ends of the tubes 214 a distance sufficient to accomplish the movement of the movable cannula structure required to open the gripping and releasing mechanism 14 to the maximum extent. At the proximal ends of the three movable wire sections 22, a piston rod section 236 provides a continuation of the movable cannula structure which is connected by heat shrinking the heat shrinkable sleeve in surround relation thereto. The heat shrinkable sleeve may be formed of a wide variety of plastic materials, such as (polyethylene, polyester, nylon, a preferred material being polytetraflourethylene for its desirable frictionless characteristics.

The heat shrinkable sleeve is shown in heat shrunken condition as a heat shrunken sleeve 238 in FIG. 30 disposed in surrounding relation adhered to the movable wire sections 22 and the piston rod section 236.

The piston rod section 236 extends beyond the proximal end of the heat shrunken sleeve 238 and has a spring biased piston member 240 formed integrally at its proximal end. Preferably, the entire integral part comprising the piston rod section 236 and piston member 240 is formed of metal, e.g. stainless steel. It is connected into (1) the handpiece assembly 16 in place of the inner metal tube 56 and piston element. The single lumen tubular member 228 is disposed in surrounding relation to the heat shrunken sleeve 238. The proximal end portion of the single lumen member 228 is connected in (1) the handpiece assembly 16 in place of the outer metal tube 56 and (2) the handpiece assembly 128 in place of the outer metal tube 186.

It is also within the contemplation of the present invention to utilize the slidably cooperating single lumen tubular member 228 and heat shrunken sleeve 238 as the entire fixed and movable parts of the cannula assembly 12. This modification involves simply the elimination of the covered proximal portions 224 of the coils 220 and spacing the distal end of the heat shrunken sleeve 238 from the proximal ends of the elastomeric covered coils 220–222 at the proximal end of the joint of the gripping and releasing mechanism 14.

In this embodiment, the distal end portion of the single lumen tubular member 228 enters into the joint at the proximal end of the gripping and releasing assembly 14 by first inserting the distal end portion of the single lumen tubular member 228 over the extending tubular elements 28 and then heat shrinking a short heat shrinkable tube (not shown) thereover so that the distal end of the single lumen tubular member 228 molds the soften thermoplastic material in adhered contact as aforesaid. Thereafter, the heat shrunken tube (not shown) is stripped from the joint in accordance with known procedures.

In this embodiment, as well as the one shown in FIG. 2, the entire tubular structures 214 or the proximal portions 220–224 thereof could be replaced by polymide or Peek tubes.

It thus will be seen that the objects of this invention have been fully and effectively accomplished. It will be realized, however, that the foregoing preferred embodiments of the present invention have been shown and described for the purposes of illustrating the structural and functional principles of the present invention and are subject to change without departure from the spirit and scope of the appended claims.

The invention claimed is:

1. In a medical extractor comprising:
   an elongated cannula assembly having a distal end constructed and arranged to be inserted into a patient and a proximal end constructed and arranged to be retained exteriorly of the patient,
   said cannula assembly having an annularly expanding and retracting gripping and releasing mechanism at the distal end thereof and a moving assembly at the proximal end thereof,
   said gripping and releasing mechanism including an annular series of longitudinally fixed flexure elements and a corresponding series of longitudinally movable flexure elements,
   said fixed flexure elements being fixed relatively together in an annular array at a confining fixed position and having a flexure position spaced longitudinally outwardly therefrom,
   each of said fixed flexure elements being constructed and arranged to flex at the flexure position thereof transversely outwardly and inwardly about the confined fixed position thereof,
   each of said movable flexure elements having an end fixed with respect to the flexure position of one of said fixed flexure elements and extending therefrom in longitudinally movable and generally transversely confined relation to a receiving portion of an adjacent fixed flexure element the longitudinal outer end of which is adjacent the flexure position thereof,
   said moving assembly and said cannula assembly being constructed and arranged so that a manual movement of said moving assembly in one direction will effect a movement of said movable flexure elements in an outward direction with respect to the receiving portions associated therewith to extend in an arcuately flexed condition beyond the flexure positions of said fixed flexure elements to cause the latter to flex transversely outwardly and create an expanded condition defined by an annular series of transversely outwardly flexed fixed flexure elements interconnected by an annular series of arcuately flexed portions of said movable flexure elements,
   said moving assembly and said cannula assembly being constructed and arranged so that a manual movement of said moving assembly in an opposite direction will effect a movement of said movable flexure elements when in said expanded condition in a direction inwardly with respect to the receiving portions associated therewith to cause said expanded condition to progressively retract during which the annular series of transversely outwardly flexed fixed flexure elements are progressively less flexed transversely outwardly and the annular series of arcuately flexed portions of said movable flexure elements have a progressively less arcuate extent,
   the improvement which comprises said fixed flexure elements being self-biased to move toward the expanded condition thereof so as to aid the movement thereto by said movable flexure elements.

2. In an annularly expanding and retracting gripping and releasing mechanism comprising:

an annular series of longitudinally fixed flexure elements and a corresponding series of longitudinally movable flexure elements;

said fixed flexure elements being fixed relatively together in an annular array at a confining fixed position and having a flexure position spaced longitudinally outwardly therefrom;

each of said fixed flexure elements being constructed and arranged to flex at the flexure position thereof transversely outwardly and inwardly about the confined fixed position thereof;

each of said movable flexure elements having an end fixed with respect to the flexure position of one of said fixed flexure elements and extending therefrom in longitudinally movable and generally transversely confined relation to a receiving portion of an adjacent fixed flexure element the outer end of which is adjacent the flexure position thereof;

said movable flexure elements being constructed and arranged to be moved longitudinally in an outward direction with respect to the receiving portions associated therewith to extend in an arcuately flexed condition generally beyond the flexure positions of said fixed flexure elements to cause the latter to flex transversely outwardly and create an expanded condition defined by an annular series of transversely outwardly flexed fixed fixture elements interconnected by an annular series of arcuately flexed portions of said movable flexure elements;

said movable flexure elements being constructed and arranged to be moved when in said expanded condition in a direction inwardly with respect to the receiving portions associated therewith to cause said expanded condition to progressively retract during which the annular series of transversely outwardly flexed fixed flexure elements are progressively less flexed transversely outwardly and the annular series of arcuately flexed portions of said movable flexure elements have a progressively less arcuate extent,

* * * * *